US009567641B2

(12) United States Patent
Kim et al.

(10) Patent No.: US 9,567,641 B2
(45) Date of Patent: Feb. 14, 2017

(54) COMBINATION THERAPY FOR THE TREATMENT OF CANCER USING AN ANTI-C-MET ANTIBODY

(71) Applicants: SAMSUNG ELECTRONICS CO., LTD., Suwon-si, Gyeonggi-do (KR); GEORGETOWN UNIVERSITY, Washington, DC (US)

(72) Inventors: Bo Gyou Kim, Seoul (KR); Shangzi Wang, Washington, DC (US); Ji Min Lee, Seoul (KR); Kyung Ah Kim, Seongnam-si (KR); Louis M. Weiner, Washington, DC (US)

(73) Assignees: SAMSUNG ELECTRONICS CO., LTD., Suwon-si (KR); GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 14/323,642

(22) Filed: Jul. 3, 2014

(65) Prior Publication Data

US 2015/0010575 A1    Jan. 8, 2015

Related U.S. Application Data

(60) Provisional application No. 61/842,762, filed on Jul. 3, 2013.

(30) Foreign Application Priority Data

Jun. 30, 2014 (KR) .......................... 10-2014-0081025

(51) Int. Cl.

| | | |
|---|---|---|
| A61K 39/395 | (2006.01) |
| C12Q 1/68 | (2006.01) |
| A61K 45/06 | (2006.01) |
| A61K 38/18 | (2006.01) |
| G01N 33/50 | (2006.01) |
| C07K 16/28 | (2006.01) |
| A61K 38/08 | (2006.01) |
| A61K 38/10 | (2006.01) |
| A61K 38/17 | (2006.01) |

(52) U.S. Cl.
CPC ............. *C12Q 1/6886* (2013.01); *A61K 38/08* (2013.01); *A61K 38/10* (2013.01); *A61K 38/1774* (2013.01); *A61K 38/1808* (2013.01); *A61K 39/39558* (2013.01); *A61K 45/06* (2013.01); *C07K 16/2836* (2013.01); *G01N 33/5011* (2013.01); *G01N 33/5023* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,333,194 B1 | 12/2001 | Levy et al. | |
| 7,615,529 B2 * | 11/2009 | Kong-Beltran et al. ................. | C07K 16/2863 435/6.14 |
| 7,741,306 B2 | 6/2010 | Slack et al. | |
| 8,563,696 B2 | 10/2013 | Cheong et al. | |
| 2009/0012016 A1 | 1/2009 | Mourelatos et al. | |
| 2009/0220495 A1 | 9/2009 | Fanidi et al. | |
| 2010/0285001 A1 | 11/2010 | Land et al. | |
| 2010/0287628 A1 | 11/2010 | Ostertag et al. | |
| 2011/0104176 A1 | 5/2011 | Cheong et al. | |
| 2011/0239316 A1 * | 9/2011 | Goetsch ................. | C07K 16/00 800/13 |
| 2013/0072389 A1 | 3/2013 | Penny et al. | |
| 2014/0141986 A1 | 5/2014 | Spetzler et al. | |
| 2014/0148350 A1 | 5/2014 | Spetzler et al. | |
| 2014/0162888 A1 | 6/2014 | Kuslich et al. | |

FOREIGN PATENT DOCUMENTS

| | | |
|---|---|---|
| EP | 2177615 A1 | 4/2010 |
| JP | 2005-304497 A | 11/2005 |
| JP | 2008-535853 A | 9/2008 |
| KR | 2011-0047698 A | 5/2011 |
| KR | 2013-0056855 A | 5/2013 |
| WO | WO 2005/042705 A2 | 5/2005 |
| WO | WO 2006/110581 A2 | 10/2006 |
| WO | WO 2010/040571 A2 | 4/2010 |
| WO | WO 2013/059496 A1 | 4/2013 |

OTHER PUBLICATIONS

Kong-Beltran et al, Cancer Cell, 2004, 6:75-84.*
Rudikoff et al. (Proc Natl Acad Sci USA 1982 vol. 79 p. 1979).*
MacCallum et al. J. Mol. Biol. (1996) 262: 732-745.*
Xu et al (Immunity, 2000, 13:37-45).*
Casset et al. (BBRC 2003, 307:198-205).*
Bani et al (Molecular Cancer Therapeutics, 2004, 3:111-121).*
Kong-Beltran et al (Cancer Cell, 2004, 6:75-84).*
Straussman et al., Tumour micro-environment elicits innate resistance to RAF inhibitors through HGF secretion, *Nature*, 487:500-504 (2012).
Basilico et al., Four individually druggable MET hotspots mediate HGF-driven tumor progression, *J. Clin. Invest.*, 124(7):3172-3186 (2014).

* cited by examiner

*Primary Examiner* — Laura B Goddard
(74) *Attorney, Agent, or Firm* — Leydig, Voit & Mayer, Ltd.

(57) ABSTRACT

A target substance used for combination treatment with an anti-c-Met antibody, a pharmaceutical composition for combination administration for preventing and/or treating cancer including an anti-c-Met antibody and an inhibitor against the target substance as active ingredients, a method for preventing and/or treating cancer including co-administering an anti-c-Met antibody and an inhibitor against the target substance, and a method for screening a drug for preventing and/or treating cancer using the target substance.

6 Claims, 11 Drawing Sheets
(1 of 11 Drawing Sheet(s) Filed in Color)

MKN45-L3-1Y/IgG2
resistant clone#1

COMBINATION THERAPY FOR THE TREATMENT OF CANCER USING AN ANTI-C-MET ANTIBODY

CROSS-REFERENCE TO RELATED APPLICATIONS

This application claims the benefits of U.S. Provisional Patent Application No. 61/842,762 filed on Jul. 3, 2013 and Korean Patent Application No. 10-2014-0081025 filed on Jun. 30, 2014 in the Korean Intellectual Property Office, the entire disclosures of which are hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 136,687 Bytes ASCII (Text) file named "716906 ST25_REV.TXT," created on Sep. 21, 2015.

BACKGROUND

1. Field

Disclosed herein is a target substance used for combination treatment with an anti-c-Met antibody, a pharmaceutical composition for combination administration for preventing and/or treating cancer including an anti-c-Met antibody and an inhibitor against the target substance as active ingredients, a method for preventing and/or treating cancer including co-administering an anti-c-Met antibody and an inhibitor against the target substance, and a method for screening a drug for preventing and/or treating cancer using the target substance.

2. Description of the Related Art

According to recent research, anticancer drugs having a specific target have been known to have a higher chance of showing acquired resistance than anticancer drugs having no specific targets (Nature, 487, 500-504). Measures for preventing resistance generated by the targeted anticancer drugs and for maximizing the efficacy of the anticancer drugs by suppressing factors that cause resistance against the targeted anticancer drugs are being developed. Also, there are often cases that the targeted anticancer drugs have a limited scope of application, and it is possible to expand their scope of application by co-administrating them together with an inhibitor of other factors. Further, by virtue of such co-administration, the amount of the anticancer drugs to be administered can be decreased by enhancing the efficacy of the anticancer drugs. Through this, it is possible to maximize anticancer efficacy while minimizing the toxicity and/or side effects of anticancer drugs upon each and every organ of a body.

Accordingly, in combination therapy using the pre-existing targeted anticancer drugs, it is necessary to select a secondary target with excellent combination treatment effects.

SUMMARY

Provided is a pharmaceutical composition including an anti-c-Met antibody and an inhibitor against the target substance.

Also provided is a method of preventing and/or treating cancer including co-administering an anti-c-Met antibody and an inhibitor against the target substance to a subject in need of preventing and/or treating cancer.

Further provided is a method for screening for a drug that prevents or treats cancer using the target substance.

Additionally, a method for selecting a subject to which an anti-c-Met antibody may be applied is provided herein, the method including measuring the level of the target substance in a specimen obtained from a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
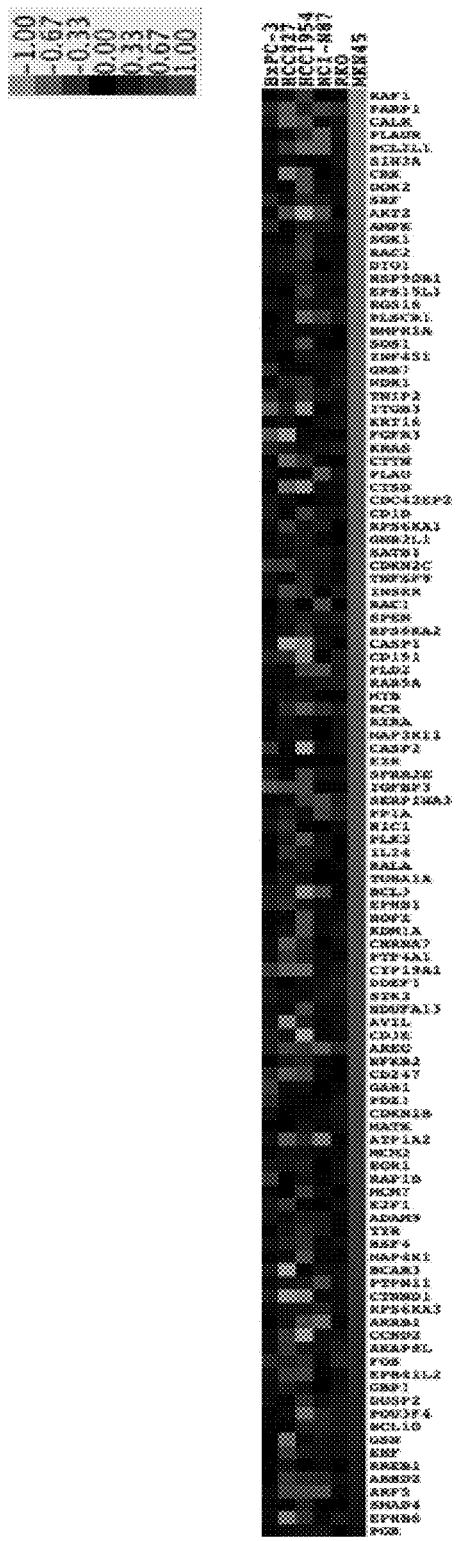
FIG. 1 is a chart depicting Log 2 value (SI value) in a variety of cell lines as a hitmap.

Research indicates it is possible to prevent resistance against c-Met-targeted drugs as well as to bring about synergistic effects by inhibiting several specific factors together with the inhibition of c-Met protein by c-Met-targeted drug treatment. Further it can lead to treatment effects even in cancer that do not exhibit treatment effects by a c-Met-targeted drug alone and reduce the dose of each drug due to synergistic effects, thereby causing a decline in side effects. Thus, it is intended in the invention to provide the specific factors as a secondary target for co-administration with c-Met-targeted drugs, for example, an anti-c-Met antibody.

More particularly, an anti-c-Met antibody has been generally known to be highly effective in c-Met addicted cells that show c-Met pathway dependent cell growth and generally express high amounts of c-Met. For example, c-Met amplification is mostly found in gastric cancer and lung cancer and in the case of colorectal cancer, it is not shown in a primary cancer but if it is metastasized to liver, it turns up at a high ratio, and the anti-c-Met antibody is considered to be particularly effective to cancers showing such c-Met amplification. However, by combination therapy where the anti-c-Met antibody is administered with an inhibitor against the aforementioned secondary target, therapeutic efficacy can be exhibited in other cancers on which the anti-c-Met antibody alone has no effects, besides the cancers having c-Met amplification, so that an application range of the anti-c-Met antibody can be extended and it is also advantageous to overcome resistance against the anti-c-Met antibody. Furthermore, in connection with the administration to the cancers on which the anti-c-Met antibody has already an effect, the amount of anticancer drugs to be administered can be effectively reduced by the combination therapy and, through this, it is possible to maximize anticancer efficacy while minimizing any side effects that might occur in a subject.

Hence, combination treatment targets enabling an increase in the efficacy of the anti-c-Met antibody were searched. The term "synthetic lethality" used in genetics refers to when a combination of mutations leads to apoptosis, whereas individual mutation alone does not affect cell viability. A screening of genes that increase the efficacy of an anticancer drug (synthetic lethal screening) is often conducted by applying the phenomenon where apoptosis is caused by such co-presence. The targets selected therefrom are applicable as combination administration measures for increasing the therapeutic efficacy of anticancer drugs.

In this invention, to search genes which increase the efficacy of the anti-c-Met antibody, genes that enhance the efficacy of the anti-c-Met antibody when suppressed together with the treatment of the anti-c-Met antibody were screened using siRNA library of 1310 genes. In other words, by selecting siRNAs which enhance the anticancer efficacy of the anti-c-Met antibody when co-treated with the anti-c-Met antibody, genes that the siRNAs inhibit were chosen. As a result, 111 genes as set forth in the following Table 1 were chosen.

TABLE 1

| GeneSymbol | EntrezGene |
|---|---|
| ABHD2 | 11057 |
| ADAM9 | 8754 |
| AKAP8L | 26993 |
| AKT2 | 208 |
| AMPK | 5564 |
| AREG | 374 |
| ARF5 | 381 |
| ARRB1 | 408 |
| ATP1A2 | 477 |
| AVIL | 10677 |
| BCAR3 | 8412 |
| BCL10 | 8915 |
| BCL2L1 | 598 |
| BCL3 | 602 |
| BCR | 613 |
| BMPR1A | 657 |
| CALR | 811 |
| CASP1 | 834 |
| CASP2 | 835 |
| CCND2 | 894 |
| CD151 | 977 |
| CD1D | 912 |
| CD247 | 919 |
| CD3E | 916 |
| CDC42EP2 | 10435 |
| CDKN1B | 1027 |
| CDKN2C | 1031 |
| CHRNA7 | 1139 |
| CRK | 1398 |
| CTNND1 | 1500 |
| CTSD | 1509 |
| CTTN | 2017 |
| CYP19A1 | 1588 |
| DDEF1 | 50807 |
| DIO1 | 1733 |
| DOK2 | 9046 |
| DUSP2 | 1844 |
| E2F1 | 1869 |
| EGR1 | 1958 |
| EHF | 26298 |
| EPB41L2 | 2037 |
| EPHB1 | 2047 |
| EPHB6 | 2051 |
| EPS15L1 | 58513 |
| EZR | 7430 |
| FGFR3 | 2261 |
| FOS | 2353 |
| GAB1 | 2549 |
| GBP1 | 2633 |
| GNB2L1 | 10399 |
| GRB7 | 2886 |
| GSN | 2934 |
| HIC1 | 3090 |
| HOPX | 84525 |
| HSF4 | 3299 |
| HSP90B1 | 7184 |
| IGFBP3 | 3486 |
| IL24 | 11009 |
| INSRR | 3645 |
| ITGB3 | 3690 |
| KDM1A | 23028 |
| KRAS | 3845 |
| KRT16 | 3868 |
| MAP3K11 | 4296 |
| MAP4K1 | 11184 |
| MATK | 4145 |
| MCM2 | 4171 |
| MCM7 | 4176 |
| MYB | 4602 |
| NDUFA13 | 51079 |
| NFKB2 | 4791 |
| PARP1 | 142 |
| PDX1 | 3651 |
| PGR | 5241 |
| PLAU | 5328 |
| PLAUR | 5329 |
| PLD2 | 5338 |
| PLK2 | 10769 |

TABLE 1-continued

| GeneSymbol | EntrezGene |
| --- | --- |
| PLSCR1 | 5359 |
| POU3F4 | 5456 |
| PPIA | 5478 |
| PTP4A1 | 7803 |
| PTPN11 | 5781 |
| RAB5A | 5868 |
| RAC1 | 5879 |
| RAC2 | 5880 |
| RAF1 | 5894 |
| RALA | 5898 |
| RAP1B | 5908 |
| RGS16 | 6004 |
| RPS6KA1 | 6195 |
| RPS6KA2 | 6196 |
| RPS6KA3 | 6197 |
| RREB1 | 6239 |
| RXRA | 6256 |
| SATB1 | 6304 |
| SERPINA3 | 12 |
| SGK1 | 6446 |
| SIN3A | 25942 |
| SMAD4 | 4089 |
| SOS1 | 6654 |
| SPEN | 23013 |
| SPRR2E | 6704 |
| SRF | 6722 |
| STK3 | 6788 |
| TNFSF9 | 8744 |
| TNIP2 | 79155 |
| TUBA1A | 7846 |
| TYR | 7299 |
| WDR1 | 9948 |
| ZNF451 | 26036 |

The genes set forth in the above are searchable through EntrezGene numbers contained in NCBI database (http://www.ncbi.nlm.nih.gov/).

Therefore, one aspect of the disclosure provides a target substance as a secondary target for combination treatment using an anti-c-Met antibody, including at least one selected from the group consisting of genes set forth in above Table 1 and proteins encoded by the genes.

Throughout the specification, the term 'secondary target' is used to refer to a gene or a protein which becomes an inhibitory object together, besides the c-Met protein (primary target) at which the anti-c-Met antibody is targeted, in combination treatment using the anti-c-Met antibody.

The term 'target substance' in the specification is used to refer to a biomarker such as a gene, or a protein encoded by the gene which becomes a target besides the c-Met protein in combination treatment using the anti-c-Met antibody.

By inhibiting the target substances as secondary targets for combination treatment using the anti-c-Met antibody chosen in the above along with the administration of the anti-c-Met antibody, the efficacy of the anti-c-Met antibody can be enhanced, anticancer effects even in cancers on which the anti-c-Met antibody alone has no effects can also occur, and resistance against the anti-c-Met antibody, for example, innate resistance, acquired resistance resulting from repetitive administration, or both can be overcome.

Another aspect provides a method for preventing and/or treating cancer including co-administering a pharmaceutically effective amount of an anti-c-Met antibody or an antigen-bonding fragment thereof and a pharmaceutically effective amount of an inhibitor against the target substance to a subject in need of prevention and/or treatment of cancer. The method may further include a step of identifying a subject who is in need of the prevention and/or treatment of cancer, prior to the administration step.

The combination administration step may be performed either by administering an anti-c-Met antibody and an inhibitor against the target substance together (at the same time) or by administering them sequentially in any order. In one embodiment, the combination administration may be performed by administering a mixture of a pharmaceutically effective amount of an anti-c-Met antibody and a pharmaceutically effective amount of an inhibitor against the target substance. In another embodiment, the combination administration may be done by performing a first step of administering a pharmaceutically effective amount of an anti-c-Met antibody and a second step of administering a pharmaceutically effective amount of an inhibitor against the target substance simultaneously or sequentially. In the case of sequential administration, it can be performed in any order.

The subject may be mammals such as primates including humans and monkeys, and rodents including mice and rats, or cells or tissues isolated from the living body thereof.

Another aspect provides a pharmaceutical composition for combination administration for preventing and/or treating cancer including an anti-c-Met antibody and an inhibitor against the target substance as active ingredients.

In one embodiment, the pharmaceutical composition for combination administration may be in a form for simultaneous administration of two drugs including a mixture of a pharmaceutically effective amount of an anti-c-Met antibody and a pharmaceutically effective amount of an inhibitor against the target substance.

In another embodiment, the pharmaceutical composition for combination administration may be in a form of simultaneous or sequential administration of a pharmaceutically effective amount of an anti-c-Met antibody and a pharmaceutically effective amount of an inhibitor against the target substance being individually formulated. In this case, the pharmaceutical composition for combination administration may be a pharmaceutical composition for combination administration for simultaneous or sequential administration including a first pharmaceutical composition containing a pharmaceutically effective amount of an anti-c-Met antibody and a second pharmaceutical composition containing a pharmaceutically effective amount of an inhibitor against the target substance. In the case of sequential administration, it can be performed in any order.

Another aspect provides a kit for preventing and/or treating cancer, including a first pharmaceutical composition containing a pharmaceutically effective amount of an anti-c-Met antibody, a second pharmaceutical composition containing a pharmaceutically effective amount of an inhibitor against the target substance, and a package container.

Another aspect provides a use of combination administration of an anti-c-Met antibody and an inhibitor against the target substance for preventing and/or treating cancer. Another aspect provides a use of the target substance as a secondary target in combination treatment using an anti-c-Met antibody.

In accordance with the disclosure, by co-administering an anti-c-Met antibody and an inhibitor against the target substance, excellent synergistic effects can be achieved in comparison with the use of the anti-c-Met antibody alone and further, even when administration concentrations are decreased and/or administration intervals are increased, at least equivalent effects can be obtained in comparison with the use of a single drug, and side effects against the anti-c-Met antibody can be minimized, and excellent anticancer effects can be obtained even in cancers which shows agonism with regard to the anti-c-Met antibody and/or cancers on which the anti-c-Met antibody has no effects so that diseases for which the anti-c-Met antibody is efficacious can be expanded.

The inhibitors of the target substances may be any compounds capable of inhibiting the expression and/or activity of one or more target substances selected from the group consisting of genes set forth in Table 1 and proteins encoded by them. For example, when the target substances are genes, the inhibitors may be one or more selected from the group consisting of a chemical drug (compound), an siRNA, a microRNA, an shRNA, an aptamer, etc., against the genes, and for example, they may be one or more selected from the group consisting of an siRNA, microRNA, shRNA, and aptamer that is capable of hybridizing with adjacent 2 to 200 bp, particularly 10 to 100 bp or 20 to 50 bp regions within the nucleotide sequences of the above genes. The 'capable of hybridizing' or 'hybridizable' refers to when complementary binding is possible by having sequence homology of at least 80%, for example at least 90%, at least 95%, at least 98%, at least 99%, or 100% to the nucleotide sequences of the above gene regions. Also, when the target substances are proteins, the inhibitors may be one or more selected from the group consisting of a chemical drug (compound), an antibody, an aptamer, etc.

For illustration purposes, siRNAs and inhibitors available to inhibit the target substances of Table 1 are listed in the following Table 2 and Table 3 (the siRNAs for the target substances in Table 2 below are searchable through catalog numbers contained in Qiagen homepage (http://www.qiagen.com)).

TABLE 2 siRNAs for Target Substances

| GeneSymbol | EntrezGene | Validated siRNA Catalog | |
|---|---|---|---|
| ABHD2 | 11057 | SI03140557 | SI03242806 |
| ADAM9 | 8754 | SI00056301 | SI00056308 |
| AKAP8L | 26993 | SI02622347 | SI02758987 |
| AKT2 | 208 | SI00299166 | SI00299173 |
| AMPK | 5564 | SI00086429 | SI02622242 |
| AREG | 374 | SI00299852 | SI00299936 |
| ARF5 | 381 | SI00300300 | SI03242351 |
| ARRB1 | 408 | SI02643977 | SI02776921 |
| ATP1A2 | 477 | SI00306495 | SI03054422 |
| AVIL | 10677 | SI00308476 | SI04262489 |
| BCAR3 | 8412 | SI00053102 | SI03081603 |
| BCL10 | 8915 | SI00057778 | SI03063144 |
| BCL2L1 | 598 | SI00023191 | SI03112018 |
| BCL3 | 602 | SI00073283 | SI03082156 |
| BCR | 613 | SI00288141 | SI04713422 |
| BMPR1A | 657 | SI02659622 | SI04434388 |
| CALR | 811 | SI02777096 | SI03053491 |
| CASP1 | 834 | SI02661932 | SI02662443 |
| CASP2 | 835 | SI02625546 | SI03025491 |
| CCND2 | 894 | SI00027832 | SI03071369 |
| CD151 | 977 | SI00063105 | SI02777257 |
| CD1D | 912 | SI00027916 | SI00027923 |
| CD247 | 919 | SI00014448 | SI00014462 |
| CD3E | 916 | SI02624230 | SI03055598 |
| CDC42EP2 | 10435 | SI00341089 | SI04348491 |
| CDKN1B | 1027 | SI02621990 | SI02621997 |
| CDKN2C | 1031 | SI00605080 | SI00605087 |
| CHRNA7 | 1139 | SI00014700 | SI03056893 |
| CRK | 1398 | SI00073780 | SI00073794 |
| CTNND1 | 1500 | SI00025382 | SI02626001 |
| CTSD | 1509 | SI00029813 | SI03097521 |
| CTTN | 2017 | SI02662485 | SI02661960 |
| CYP19A1 | 1588 | SI00002030 | SI00002044 |
| DDEF1 | 50807 | SI00360591 | SI04181800 |
| DIO1 | 1733 | SI00015764 | SI00015778 |
| DOK2 | 9046 | SI03025344 | SI03104346 |
| DUSP2 | 1844 | SI03024469 | SI04892692 |

TABLE 2-continued siRNAs for Target Substances

| GeneSymbol | EntrezGene | Validated siRNA Catalog | |
|---|---|---|---|
| E2F1 | 1869 | SI00300083 | SI02664410 |
| EGR1 | 1958 | SI03052511 | SI03078950 |
| EHF | 26298 | SI04165805 | SI04283363 |
| EPB41L2 | 2037 | SI00380247 | SI04234139 |
| EPHB1 | 2047 | SI00063742 | SI02223557 |
| EPHB6 | 2051 | SI02665292 | SI02758441 |
| EPS15L1 | 58513 | SI00130403 | SI03058398 |
| EZR | 7430 | SI00302162 | SI02664228 |
| FGFR3 | 2261 | SI00002968 | SI00604772 |
| FOS | 2353 | SI00074543 | SI02781464 |
| GAB1 | 2549 | SI00031913 | SI03077403 |
| GBP1 | 2633 | SI04179595 | SI04183578 |
| GNB2L1 | 10399 | SI00084497 | SI02636662 |
| GRB7 | 2886 | SI00075607 | SI03083381 |
| GSN | 2934 | SI02664039 | SI02664046 |
| HIC1 | 3090 | SI00088970 | SI02656031 |
| HOPX | 84525 | SI03156517 | SI04323599 |
| HSF4 | 3299 | SI00442652 | SI00442659 |
| HSP90B1 | 7184 | SI02663738 | SI02655177 |
| IGFBP3 | 3486 | SI02623880 | SI02780589 |
| IL24 | 11009 | SI00092442 | SI02638139 |
| INSRR | 3645 | SI00103628 | SI00103635 |
| ITGB3 | 3690 | SI00004585 | SI02623159 |
| KDM1A | 23028 | SI00109102 | SI02781177 |
| KRAS | 3845 | SI00071015 | SI02662051 |
| KRT16 | 3868 | SI00464471 | SI00464485 |
| MAP3K11 | 4296 | SI02659552 | SI04435851 |
| MAP4K1 | 11184 | SI00095130 | SI02224257 |
| MATK | 4145 | SI00605605 | SI00605598 |
| MCM2 | 4171 | SI00064918 | SI02653525 |
| MCM7 | 4176 | SI00629104 | SI04307534 |
| MYB | 4602 | SI00076230 | SI00076237 |
| NDUFA13 | 51079 | SI00430934 | SI04249749 |
| NFKB2 | 4791 | SI00300965 | SI04224290 |
| PARP1 | 142 | SI02662989 | SI02662996 |
| PDX1 | 3651 | SI00448035 | SI04288165 |
| PGR | 5241 | SI00018690 | SI00018704 |
| PLAU | 5328 | SI02662135 | SI02662674 |
| PLAUR | 5329 | SI03033289 | SI03048458 |
| PLD2 | 5338 | SI00041244 | SI03020857 |
| PLK2 | 10769 | SI04438770 | SI04438777 |
| PLSCR1 | 5359 | SI00129332 | SI03075751 |
| POU3F4 | 5456 | SI00006748 | SI03077410 |
| PPIA | 5478 | SI00690914 | SI04351718 |
| PTP4A1 | 7803 | SI00052213 | SI03065118 |
| PTPN11 | 5781 | SI00044002 | SI02225909 |
| RAB5A | 5868 | SI02655037 | SI02632602 |
| RAC1 | 5879 | SI03065531 | SI02655051 |
| RAC2 | 5880 | SI00044947 | SI02655058 |
| RAF1 | 5894 | SI00301623 | SI02223032 |
| RALA | 5898 | SI00076594 | SI02662835 |
| RAP1B | 5908 | SI00111769 | SI02662303 |
| RGS16 | 6004 | SI03063760 | SI03069178 |
| RPS6KA1 | 6195 | SI02223060 | SI02223067 |
| RPS6KA2 | 6196 | SI02225006 | SI04379487 |
| RPS6KA3 | 6197 | SI00288190 | SI00288197 |
| RREB1 | 6239 | SI03195605 | SI04264995 |
| RXRA | 6256 | SI00046130 | SI00046144 |
| SATB1 | 6304 | SI00046298 | SI00046319 |
| SERPINA3 | 12 | SI00715519 | SI00715526 |
| SGK1 | 6446 | SI00079688 | SI00287798 |
| SIN3A | 25942 | SI00719068 | SI02781240 |
| SMAD4 | 4089 | SI00076020 | SI00076041 |
| SOS1 | 6654 | SI00079793 | SI00079807 |
| SPEN | 23013 | SI03077697 | SI02641128 |
| SPRR2E | 6704 | SI02821574 | SI02821588 |
| SRF | 6722 | SI02757622 | SI03034731 |
| STK3 | 6788 | SI02622256 | SI02622263 |
| TNFSF9 | 8744 | SI03036684 | SI03096576 |
| TNIP2 | 79155 | SI00748769 | SI04174037 |
| TUBA1A | 7846 | SI00753298 | SI00753305 |
| TYR | 7299 | SI04255055 | SI04308136 |
| WDR1 | 9948 | SI00761712 | SI03122448 |
| ZNF451 | 26036 | SI04152232 | SI04237191 |

TABLE 3

Inhibitors of Target Substances

| Target | Inhibitor |
|---|---|
| AKT2 | MK-2206 (8-(4-(1-aminocyclobutyl)phenyl)-9-phenyl-[1,2,4]triazolo[3,4-f][1,6]naphthyridin-3(2H)-one) |
| AMPK | Dorsomorphin dihydrochloride (6-[4-[2-(1-Piperidinyl)ethoxy]phenyl]-3-(4-pyridinyl)-pyrazolo[1,5-a]pyrimidine dihydrochloride) |
| BCL2L1 | ABT-263 (Navitoclax) (4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide) |
| BCR | Imatinib (4-[(4-methylpiperazin-1-yl)methyl]-N-(4-methyl-3-{[4-(pyridin-3-yl)pyrimidin-2-yl]amino}phenyl)benzamide) |
| Caspase-2 | Caspase-2 inhibitor (e.g., peptide VDVAD or derivatives thereof; e.g., Ac-VDVAD-CHO, Z-VDVAD-FMK (N-Benzyloxycarbonyl-Val-Asp(OMe)-Val-Ala-Asp(OMe)-fluoromethyl ketone), etc.) |
| CRK | Cdk/Crk inhibitor (e.g., CAS 784211-09-2; 1-(2,6-Dichlorophenyl)-1,5-dihydro-6-((4-(2-hydroxyethoxy)phenyl)methyl)-3-(1-methylethyl)-4H-pyrazolo[3,4-d]pyrimidin-4-one, etc.) |
| Dkk-1 | Dkk-1 inhibitor (e.g., WAY-262611; (1-(4-(Naphthalen-2-yl)pyrimidin-2-yl)piperidin-4-yl)methanamine, etc.) |
| Ezrin | Ezrin inhibitor (e.g., NSC668394; 7-(3,5-dibromo-4-hydroxyphenethylamino)quinoline-5,8-dione, etc.) |
| FGFR3 | PD173074 (1-tert-butyl-3-(2-(4-(diethylamino)butylamino)-6-(3,5-dimethoxyphenyl)pyrido[2,3-d]pyrimidin-7-yl)urea) |
| FGFR3 | Masitinib (4-[(4-Methylpiperazin-1-yl)methyl]-N-(4-methyl-3-{[4-(pyridin-3-yl)-1,3-thiazol-2-yl]amino}phenyl)benzamide) |
| FGFR3 | Dovitinib (1-amino-5-fluoro-3-(6-(4-methylpiperazin-1-yl)-1H-benzo[d]imidazol-2-yl)quinolin-2(1H)-one) |
| FGFR3 | Pazopanib (5-[[4-[(2,3-Dimethyl-2H-indazol-6-yl)methylamino]-2-pyrimidinyl]amino]-2-methylbenzsulfonamide) |
| ITGB3 | Cilengitide (EMD121974; Cyclo(L-arginylglycyl-L-α-aspartyl-D-phenylalanyl-N-methyl-L-valyl) |
| LSD1 | LSD1 inhibitor II (e.g., S2101; 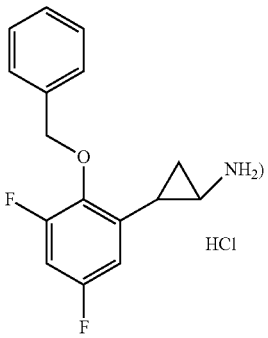 |
| NFKB2 | RO-106-9920 (6-(Phenylsulfinyl)tetrazolo[1,5-b]pyridazine) |
| PARP1 | NU1025 (8-Hydroxy-2-methyl-4(3H)-quinazolinone) |
| PARP1 | Iniparib (4-iodo-3-nitrobenzamide) |
| PARP1 | Veliparib (ABT-888; 2-((R)-2-Methylpyrrolidin-2-yl)-1H-benzimidazole-4-carboxamide) |
| PARP1 | INO-1001 (3-aminobenzamide) |
| PARP1 | Olaparib (4-[(3-[(4-cyclopropylcarbonyl)piperazin-4-yl]carbonyl)-4-fluorophenyl]methyl(2H)phthalazin-1-one) |
| PLD2 | VU 0364739 (N-[2-[1-(3-Fluorophenyl)-4-oxo-1,3,8-triazaspiro[4.5]dec-8-yl]ethyl]-2-naphthalenecarboxamide) |
| PLD2 | FIPI hydrochloride hydrate (5-Fluoro-2-indolyl des-chlorohalopemide hydrochloride hydrate) |
| PLK2 | BI-2536 ((R)-4-(8-cyclopentyl-7-ethyl-5-methyl-6-oxo-5,6,7,8-tetrahydropteridin-2-ylamino)-3-methoxy-N-(1-methylpiperidin-4-yl)benzamide) |
| PLK2 | Volasertib (BI-6727; N-((1r,4r)-4-(4-(cyclopropylmethyl)piperazin-1-yl)cyclohexyl)-4-((R)-7-ethyl-8-isopropyl-5-methyl-6-oxo-5,6,7,8-tetrahydropteridin-2-ylamino)-3-methoxybenzamide) |
| RAF1 | Sorafenib (4-[4-[[4-chloro-3-(trifluoromethyl)phenyl]carbamoylamino]phenoxy]-N-methyl-pyridine-2-carboxamide) |
| RAF1 | PLX-4720 (N-(3-(5-chloro-1H-pyrrolo[2,3-b]pyridine-3-carbonyl)-2,4-difluorophenyl)propane-1-sulfonamide) |
| RAF1 | Regorafenib (1-(4-chloro-3-(trifluoromethyl)phenyl)-3-(2-fluoro-4-(2-(methylcarbamoyl)pyridin-4-yloxy)phenyl)urea) |
| RAF1 | Vemurafenib (N-(3-{[5-(4-chlorophenyl)-1H-pyrrolo[2,3-b]pyridin-3-yl]carbonyl}-2,4-difluorophenyl)propane-1-sulfonamide) |
| RXRA | K-80003 ([(1Z)-5-fluoro-1-(4-isopropylbenzylidene)-2-methyl-1H-inden-3-yl]acetic acid) |
| SGK1 | GSK650394 (4-(2-(4-amino-1,2,5-oxadiazol-3-yl)-1-ethyl-7-((S)-piperidin-3-ylmethoxy)-1H-imidazo[4,5-c]pyridin-4-yl)-2-methylbut-3-yn-2-ol) |
| SPRR2E | CAY10621 (2,2-dimethyl-4S-(1-oxo-2-hexadecyn-1-yl)-1,1-dimethylethyl ester-3-oxazolidinecarboxylic acid) |
| SRF | CCG1423 (N-[2-[4(4-chlorophenyl)amino]-1-methyl-2-oxoethoxy]-3,5-bis(trifluoromethyl)-benzamide) |
| SYK | R406 (6-(5-fluoro-2-(3,4,5-trimethoxyphenylamino)pyrimidin-4-ylamino)-2,2-dimethyl-2H-pyrido[3,2-b][1,4]oxazin-3(4H)-one benzenesulfonate) |
| SYK | Fostamatinib (R935788; (6-(5-fluoro-2-(3,4,5-trimethoxyphenylamino)pyrimidin-4-ylamino)-2,2-dimethyl-3-oxo-2,3-dihydropyrido[3,2-b][1,4]oxazin-4-yl)methyl dihydrogen phosphate) |
| TUBA1A | Tubacin (N-(4-{(2R,4R,6S)-4-{[(4,5-diphenyl-1,3-oxazol-2-yl)sulfanyl]methyl}-6-[4-(hydroxymethyl)phenyl]-1,3-dioxan-2-yl}phenyl)-N'-hydroxyoctanediamide) |

In one embodiment, the available inhibitors of the target substances may be one or more selected from the group consisting of the siRNAs listed in Table 2 and the compounds listed in Table 3, but are not limited thereto.

Another aspect provides a method for enhancing the efficacy of an anti-c-Met antibody, including inhibiting one or more target substances selected from the group consisting of genes set forth in Table 1 above and proteins encoded by the genes. The subjects may be mammals for example primates including humans and monkeys, and rodents including mice and rats, and they may be cancer patients, for example, patients who require the administration of an anti-c-Met antibody. The cells may be cells isolated from the subjects or cultured by artificial means, for example, they may be cancer cells. The inhibition step may be performed by administering an inhibitor of the aforementioned target substance (for example, oral administration, or parenteral administration such as intravenous injection, subcutaneous injection, muscular injection, intraperitoneal injection, endothelial administration, local administration, intranasal administration, intrapulmonary administration, or rectal administration), but is not limited thereto.

Another aspect provides a method for screening a (candidate) drug for preventing and/or treating cancer using the target substance.

The screening method may include contacting a candidate compound to a cell specimen;

measuring the level of the target substance in the cell specimen; and comparing the level of the target substance in the cell specimen to which the candidate compound is contacted with the level of the target substance in a cell specimen to which the candidate compound is not contacted.

The comparison step may be performed by measuring the levels of the target substance respectively before and after the candidate compound is contacted (treated) with regard to the same cell specimen to compare them, or by contacting a candidate compound to some of the cell specimen and measuring the levels of the target substance in the part to which the candidate compound is contacted and in the other part to which the candidate compound is not contacted, respectively to compare them.

When the level of the target substance in the cell specimen to which the candidate compound is contacted is reduced compared to the level of the target substance in the cell specimen to which the candidate compound is not contacted (e.g., the level in the cell specimen prior to contact with the candidate compound), that is, if the candidate compound inhibits the target substance in the cell specimen, the candidate compound can be determined to be a drug for preventing and/or treating cancer.

The cell specimen may be cells isolated or cultured from a living body and for example, it may be cancer cells.

The candidate compound may be a variety of compounds, for example, selected from the group consisting of proteins, polypeptides, oligopeptides, polynucleotides, oligonucleotides, or other various chemical substances.

The measurement of a target substance level in the cell specimen may be performed by measuring using any ordinary means for a gene or protein quantitative assay, and/or by evaluating the measured results. For example, when the target substance is a gene, the gene level may be measured by using any ordinary gene quantification methods including, but not limited to, an ordinary polymerase chain reaction (PCR), FISH (fluorescent in situ hybridization), etc. using a primer hybridizable with the gene. When the target substance is a protein, it may be measured via an ordinary enzyme reaction, fluorescence, luminescence, and/or radioactivity detection using an antibody specifically binding to the target substance, aptamer, etc. and in particular, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, etc., but is not limited thereto.

The drug for preventing and/or treating cancer that was screened by the above screening method can lead to more enhanced synergistic effects by being co-administered with an anti-c-Met antibody and further, it can overcome resistance against the anti-c-Met antibody, reduce side effects due to a decline in the amount of the anti-c-Met antibody to be used, and exhibit excellent anticancer effects with regard to cancers on which the anti-c-Met antibody alone has no effects. Accordingly, the drug for preventing and/or treating cancer that was screened by the above screening method may be a drug for use in combination therapy using an anti-c-Met antibody as a co-administration partner of an anti-c-Met antibody, i.e., for combination administration together with the anti-c-Met antibody.

Also, the efficacy of the anti-c-Met antibody is increased as the level of the chosen target substance is decreased. In other words, there is a correlation between the level of the target substance and the efficacy of the anti-c-Met antibody and accordingly, the efficacy of a treatment using the anti-c-Met antibody can be predicted in proportion to the level of the target substance. For example, in cancer cells in which the chosen target substance is present at a high level, the efficacy of the anti-c-Met antibody is likely to be reduced, whereas in cancer cells in which the chosen target substance is present at a low level, the efficacy of the anti-c-Met antibody is likely to be well exhibited. Hence, by measuring the level of the target substance in a specimen (cells, tissues, etc.), it can be determined whether the specimen or a patient from which the specimen is derived is an object suitable for the application of the anti-c-Met antibody.

In this regard, another aspect provides a predictive marker for selecting an object suitable for the application of an anti-c-Met antibody, including one or more selected from the group consisting genes set forth in Table 1 above and proteins encoded by the genes. Still another aspect provides a method of identifying (selecting) a subject suitable for the application of an anti-c-Met antibody or predicting an effect of an anti-c-Met antibody, including measuring the level of at least one target substance selected from the group consisting of genes set forth in Table 1 above and proteins encoded by the genes in a specimen. The method of identifying a subject suitable for the application of an anti-c-Met antibody or predicting an effect of an anti-c-Met antibody may further include a step of determining the specimen or a patient from whom the specimen is derived to be a subject suitable for the application of the anti-c-Met antibody or determining that the anti-c-Met antibody exhibits the effect on the specimen or patient or predicting an effect of an anti-c-Met antibody, when the level of the measured target substance in the specimen is low. The specimen may be cells or tissues isolated from a living body or cultured by artificial means, for example, cancer cells (for example, cancer cells to be treated), and the patient from whom the specimen is derived may be mammals such as primates including humans and monkeys, and rodents including mice and rats. The measuring of a target substance level in the specimen may be performed by using any ordinary means for a gene or protein quantitative assay, and/or by evaluating the measured results, and detailed assay means thereof are as explained above.

As used herein, the "low level of a target substance" may be determined by comparing the level of the target substance in a specimen with that in a reference sample. The reference sample may be any one (a cell, a tissue. etc.) on which an anti-c-Met antibody has no effect or which has a resistance to an anti-c-Met antibody. For example, the reference sample may be at least one selected from the group consisting of cell lines H1373 (ATCC, CRL-5866), Caki-1 (ATCC, HTB-46), BT474 (ATCC, HTB-20), HT-29 (ATCC, HTB-38), SW620 (ATCC, CCL-227), Ls174T (ATCC, CL-188), and anti-c-Met antibody resistant cells (e.g., cells acquiring a resistance to an anti-c-Met antibody by repeated and/or consistent administration of the c-Met inhibitor). Therefore, the method of selecting (identifying) a subject for application of an anti-c-Met antibody may further include a step of comparing the level of a target substance in a specimen with that of a reference sample as described above. In this case, the method may further include a step of measuring the level of a target substance in the reference sample. The method may further include a step of determining (considering or selecting) the specimen or a patient from whom the specimen is derived as a suitable subject for application of an anti-c-Met antibody, when a target substance is absent or present at a low level in the specimen compared to that of the reference sample.

In a particular embodiment, the anti c-Met antibody may be any antibody or an antigen-binding fragment thereof recognizing a c-Met protein as an antigen. For example, the anti-c-Met antibody may be any antibody or an antigen-binding fragment that specifically binds to c-Met to induce c-Met intracellular internalization and degradation. The anti-c-Met antibody may recognize a specific region of c-Met, e.g., a specific region in the SEMA domain, as an epitope.

Unless otherwise stated, the term "anti-c-Met antibody" may be used to include not only a complete form of anti-c-Met antibodies, but also antigen-binding fragments thereof.

"c-Met" or "c-Met protein" refers to a receptor tyrosine kinase (RTK) which binds hepatocyte growth factor (HGF). c-Met may be derived from any species, particularly a mammal, for instance, primates such as human c-Met (e.g., NP_000236), monkey c-Met (e.g., Macaca mulatta, NP_001162100), or rodents such as mouse c-Met (e.g., NP_032617.2), rat c-Met (e.g., NP_113705.1), and the like. The c-Met protein may include a polypeptide encoded by the nucleotide sequence identified as GenBank Accession Number NM_000245, a polypeptide including the amino acid sequence identified as GenBank Accession Number NP_000236 or extracellular domains thereof. The receptor tyrosine kinase c-Met participates in various mechanisms, such as cancer incidence, metastasis, migration of cancer cell, invasion of cancer cell, angiogenesis, and the like.

c-Met, a receptor for hepatocyte growth factor (HGF), may be divided into three portions: extracellular, transmembrane, and intracellular. The extracellular portion is composed of an α-subunit and a n-subunit which are linked to each other through a disulfide bond, and contains a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may include the amino acid sequence of SEQ ID NO: 79, and is an extracellular domain that functions to bind HGF. A specific region of the SEMA domain, that is, a region including the amino acid sequence of SEQ ID NO: 71, which corresponds to a range from amino acid residues 106 to 124 of the amino acid sequence of the SEMA domain (SEQ ID NO: 79), is a loop region between the second and the third propellers within the epitopes of the SEMA domain. This region acts as an epitope for the anti-c-Met antibody provided in the present invention.

The term "epitope," as used herein, refers to an antigenic determinant, a part of an antigen recognized by an antibody. In one embodiment, the epitope may be a region comprising 5 or more contiguous (consecutive on primary, secondary, or tertiary structure) amino acid residues within the SEMA domain (SEQ ID NO: 79) of c-Met protein, for instance, 5 to 19 consecutive amino acid residues within the amino acid sequence of SEQ ID NO: 71. For example, the epitope may be a polypeptide including 5 to 19 contiguous amino acids selected from among partial combinations of the amino acid sequence of SEQ ID NO: 71, wherein the polypeptide includes the amino sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Thus, the anti-c-Met antibody may specifically bind to an epitope which includes 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may include:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence including 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 85, or an amino acid sequence including 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 86, or an amino acid sequence including 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and the at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
$Xaa_1$-$Xaa_2$-Tyr-Tyr-Met-Ser, wherein $Xaa_1$ is absent or Pro or Ser, and $Xaa_2$ is Glu or Asp, Formula II
(SEQ ID NO: 5)
Arg-Asn-$Xaa_3$-$Xaa_4$-Asn-Gly-$Xaa_5$-Thr, wherein $Xaa_3$ is Asn or Lys, $Xaa_4$ is Ala or Val, and $Xaa_6$ is Asn or Thr, Formula III
(SEQ ID NO: 6)
Asp-Asn-Trp-Leu-$Xaa_6$-Tyr, wherein Xaa$_6$ is Ser or Thr, Formula IV
(SEQ ID NO: 7)
Lys-Ser-Ser-Xaa$_7$-Ser-Leu-Leu-Ala-Xaa$_8$-Gly-Asn-Xaa$_9$-Xaa$_{10}$-Asn-Tyr-Leu-Ala wherein Xaa$_7$ is His, Arg, Gln, or Lys, Xaa$_8$ is Ser or Trp, Xaa$_9$ is His or Gln, and Xaa$_{10}$ is Lys or Asn, Formula V
(SEQ ID NO: 8)
Trp-Xaa$_{11}$-Ser-Xaa$_{12}$-Arg-Val-Xaa$_{13}$ wherein Xaa$_{11}$ is Ala or Gly, Xaa$_{12}$ is Thr or Lys, and Xaa$_{13}$ is Ser or Pro, and Formula VI
(SEQ ID NO: 9)
Xaa$_{14}$-Gln-Ser-Tyr-Ser-Xaa$_{15}$-Pro-Xaa$_{16}$-Thr wherein Xaa$_{14}$ is Gly, Ala, or Gln, Xaa$_{15}$ is Arg, His, Ser, Ala, Gly, or Lys, and Xaa$_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may include a heavy chain variable region comprising a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85; and a light chain variable region comprising a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89.

In one embodiment of the anti-c-Met antibody or antigen-binding fragment, the variable region of the heavy chain includes the amino acid sequence of SEQ ID NO: 17, 74, 87, 90, 91, 92, 93, or 94 and the variable resion of the light chain includes the amino acid sequence of SEQ ID NO: 18, 19, 20, 21, 75, 88, 95, 96, 97, 98, 99, or 107.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

An important consideration in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In a particular embodiment, the antigen-binding fragment may be scFv, (scFv)$_2$, scFvFc, Fab, Fab', or F(ab')$_2$, but is not limited thereto.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described in the above, for example, those including the amino acid length of 1 to 100, 2 to 50, particularly 5 to 25, and any kinds of amino acids may be included without any restrictions.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100 (U7-HC6), 101 (U6-HC7), 102 (U3-HC9), 103 (U6-HC8), or 104 (U8-HC5), or a hinge region including the amino acid sequence of SEQ ID NO: 105 (non-modified human hinge). In particular, the hinge region includes the amino acid sequence of SEQ ID NO: 100 or 101.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include all the antibodies defined in Korean Patent Publication No. 2011-0047698.

In the anti-c-Met antibody, the rest portion of the light chain and the heavy chain portion excluding the CDRs, the light chain variable region, and the heavy chain variable region as defined above, that is the light chain constant region and the heavy chain constant region, may be those from any subtype of immunoglobulin (e.g., IgA, IgD, IgE, IgG (IgG1, IgG2, IgG3, IgG4), IgM, and the like).

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the 21$^{st}$ to 240$^{th}$ positions of SEQ ID NO: 70;

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 108.

According to an embodiment, the anti-c-Met antibody may include a heavy chain including the amino acid sequence from the 18$^{th}$ to 460$^{th}$ positions of SEQ ID NO: 66 and a light chain including the sequence from the 21$^{st}$ to 240$^{th}$ positions of SEQ ID NO: 68, or a heavy chain including the amino acid sequence from the 18$^{th}$ to 460$^{th}$ positions of SEQ ID NO: 66 and a light chain including the sequence of SEQ ID NO: 108.

The polypeptide of SEQ ID NO: 70 is a light chain including human kappa (K) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

In another embodiment, the anti-c-Met antibody may include a light chain complementarity determining region including the amino acid sequence of SEQ ID NO: 106, a light chain variable region including the amino acid sequence of SEQ ID NO: 107, or a light chain including the amino acid sequence of SEQ ID NO: 108.

The mixture where a pharmaceutically effective amount of an anti-c-Met antibody or an antigen-binding fragment thereof and a pharmaceutically effective amount of an inhibitor against the target substance are mixed, the first pharmaceutical composition containing a pharmaceutically effective amount of an anti-c-Met antibody or an antigen-binding fragment thereof as an active ingredient, and the second pharmaceutical composition containing a pharmaceutically effective amount an inhibitor against the target substance as an active ingredient may be provided (or administered) along with a pharmaceutically acceptable carrier, diluent, and/or excipient.

The pharmaceutically acceptable carrier to be included in the mixture or the pharmaceutical composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, preservative, and the like.

The pharmaceutical composition, the mixture, or each active ingredient may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

The term "the pharmaceutically effective amount" as used in this specification refers to an amount of which each active ingredient can exert pharmaceutically significant effects.

For one-time administration, a pharmaceutically effective amount of an anti-c-Met antibody or an antigen-binding fragment thereof and a pharmaceutically effective amount of an inhibitor against the target substance may be prescribed in a variety way, depending on many factors including formulation methods, administration manners, ages of patients, body weight, gender, pathologic conditions, diets, administration time, administration interval, administration route, excretion speed, and reaction sensitivity. For example, the effective amount of sorafenib may be, but not limited to, in ranges of 0.001 to 100 mg/kg, or 0.02 to 10 mg/kg for one-time administration and the effective amount of the anti-c-Met antibodies or antigen binding fragments thereof may be, but not limited to, in ranges of 0.001 to 100 mg/kg, or 0.02 to 10 mg/kg for their one-time administration.

The effective amount for one-time administration may be formulated into a single formulation in a unit dosage form or formulated in suitably divided dosage forms, or it may be manufactured to be contained in a multiple dosage container. For the kit, the effective amount of the inhibitor against the target substance and the effective amount of the anti-c-Met antibodies or antigen binding fragments thereof for one-time administration (single dose) may be contained in a package container as a base unit.

The administration interval between the administrations is defined as a period between the first administration and the following administration. The administration interval may be, but is not limited to, 24 hours to 30 days (e.g., 10 hours, 15 hours, 20 hours, 1 day, 2 days, 3 days, 4 days, 5 days, 6, days, 7 days, 10 days, 14 days, 21 days, or 28 days) and particularly 7 to 14 days or so. For the combined therapy, the first pharmaceutical composition containing a pharmaceutically effective amount of an anti-c-Met antibody or an antigen-binding fragment thereof as an active ingredient, and the second pharmaceutical composition containing a pharmaceutically effective amount of an inhibitor against the target substance as an active ingredient may be co-administered in a given time interval (e.g., several minutes, several hours or several days, or several weeks) to be determined by a type of diseases, a patient's conditions, etc. For example, the first pharmaceutical composition and the second pharmaceutical composition may be simultaneously administered (administration interval within 1 minute) or sequentially administered (administration interval of 1 minute or over), and in case of sequential administration, the administration interval between the first pharmaceutical composition and the second pharmaceutical composition may be 1 to 60 minutes, particularly, 1 minute to 10 minutes, and they may be administered in any order.

The combined mixture or the pharmaceutical compositions may be a solution in oil or an aqueous medium, a suspension, a syrup, an emulsifying solution form, or they may be formulated into a form of an extract, elixirs, powders, granules, a tablet or a capsule, and they may further include a dispersing agent or a stabilizing agent for their formulation.

In particular, the pharmaceutical composition containing the anti-c-Met antibody or antigen binding fragments thereof may be formulated into an immunoliposome since it contains an antibody or an antigen binding fragment. A liposome containing an antibody may be prepared using any methods well known in the pertinent field. The immunnoliposome may be a lipid composition including phosphatidylcholine, cholesterol, and polyethyleneglycol-derived phosphatidylethanolamine, and may be prepared by a reverse phase evaporation method. For example, Fab' fragments of an antibody may be conjugated to the liposome through a disulfide-exchange reaction. A chemical drug, such as doxorubicin, may further be included in the liposome.

The pharmaceutical compositions or the method may be used for the prevention and/or treatment of a cancer. The cancer may be associated with overexpression and/or abnormal activation of c-Met. The cancer may be a solid cancer or a blood cancer. Particularly, the cancer may be at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head and neck cancers, brain cancer, and the like, but not be limited thereto. In addition, the cancer may be a cancer having a resistance (including innate resistance and acquired resistance) against an anti-c-Met antibody. For example, the cancer may be a solid cancer, such as a gastric cancer, a lung cancer, etc., which has a resistance (innate resistance or acquired resistance) against an anti-c-Met antibody.

The prevention and/or treatment effects of the cancers may include effects of not only suppressing the growth of the cancer cells but also suppressing deterioration of cancers due to migration, invasion, and metastasis thereof. Therefore, the curable cancers by the combined therapy may include both primary cancers and metastatic cancers.

The invention is directed to a combination administration method for leading to an increase in the efficacy of an anti-c-Met antibody, and a combination administration composition therefor. The following effects can be expected from the invention:

1) Efficacy can be enhanced, when compared to the sole administration of either an anti-c-Met antibody or an inhibitor against one of the aforementioned genes.

2) Administration concentrations can be decreased or administration intervals can be increased, when compared to the sole administration of either an anti-c-Met antibody or an inhibitor against one of the aforementioned genes. Through this, side effects occurring in a subject can be reduced.

3) The efficacy of an anti-c-Met antibody can be newly generated via combination administration in a cancer which shows no efficacy when administered with the anti-c-Met antibody alone. Through this, diseases for which the anti-c-Met antibody is efficacious can be expanded.

4) The combination administration of an anti-c-Met antibody and an inhibitor against one of the aforementioned genes can overcome a potential resistance that might occur by prolonged treatment of the anti-c-Met antibody.

EXAMPLES

Hereafter, the present invention will be described in detail by examples.

The following examples are intended merely to illustrate the invention and are not construed to restrict the invention.

Reference Example 1

Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1-2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 9, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™ 3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 4, below.

TABLE 4

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 5 and were converted into IgG forms. Four antibodies which were respectively produced from clones L3-1, L3-2, L3-3, and L3-5 were used in the subsequent experiments.

TABLE 5

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™ 3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as L3-1Y/IgG2.

Example 1

Synthetic Lethal Screening Using Anti-c-Met Antibody

To search genes capable of increasing efficacy when suppressed together with an anti-c-Met antibody, synthetic lethal screening was conducted using MKN45 gastric cancer cell line (JCRB, JCRB0254). The synthetic lethal screening was conducted using a total of 1310 genes related to c-Met including 638 genes of EGFR library (Science Signaling, 3, ra67).

First, 0.3 ul of RNAiMax (Life Technologies) and a mixture of two different kinds of 20 nM siRNAs (Qiagen) were added to a 96-well plate, which was incubated at a room temperature for 15 min, wherein RNAiMax and siRNAs were diluted in Opti-MEM (Life Technologies) and a total mixture volume was adjusted to reach 22 ul or so. 78 ul of MKN45 cells diluted in a 5% FBS-containing RPMI1640 medium (GIBCO) were seeded onto each well of the 96-well plate so that each well contained 5000 cells.

24 hours later after the transfection, the plate was treated with an antibody by adding 100 ul of a medium. For a control group in which no antibodies were treated, only a medium was added, and in case that an antibody was to be treated, it was treated with the antibody at a concentration corresponding to IC20 and incubated for 5 days. The L3-1Y/IgG2 antibody was used in such an amount that the final concentration thereof became 0.0625 μl/ml, which is approximately IC25~IC35 in MKN45 cells.

After 5 days, 20 ul of a diluting solution of CellTiter Blue (Promega, G8081) and HBSS at 1:1 was added to each well, which was incubated at 37° C. for 4 hours. Then, the number of cells was counted via fluorescence signals (560/590 nm), which were measured using Envision 2104 Multi-label Reader (Perkin Elmer).

Since an increase degree in the efficacy of an anti-c-Met antibody to be caused by the expression suppression of each gene was measured as a reduction in cell viability, SI (sensitization index) was calculated. The calculation formula of SI is as follows:

$$\text{Normalized viability} = \frac{\text{Sample value}}{\text{Median of negative control in each plate}}$$

$$\text{Sensitization index} = \frac{\text{Avg of normalized viability in drug-treated group}}{\text{Avg of normalized viability in medium-treated group}}$$

In other words, SI is obtained by dividing a cell viability change ratio due to siRNA in an antibody-treated group by a cell viability change ratio due to siRNA in a control group (medium treated group). As the value gets smaller, cancer cell growth inhibitory efficacy is more increased. Of the 1310 genes, a total of 137 genes of which the SI values were less than 0.85 (SI<0.85) when analyzed using FDR & Threshold method were obtained.

The 137 genes were re-screened by individual transfection of 4 kinds of siRNAs including the two siRNAs which were used in the above screening, respectively, not in a mixture form. Genes satisfying the standard of FDR & Threshold method in at least two kinds of siRNAs were selected in the same manner as above and as a result, 111 genes were selected. The thus chosen 111 genes are set forth in the following Table 6.

TABLE 6

| GeneSymbol | EntrezGene |
|---|---|
| ABHD2 | 11057 |
| ADAM9 | 8754 |
| AKAP8L | 26993 |
| AKT2 | 208 |
| AMPK | 5564 |
| AREG | 374 |
| ARF5 | 381 |
| ARRB1 | 408 |
| ATP1A2 | 477 |
| AVIL | 10677 |
| BCAR3 | 8412 |
| BCL10 | 8915 |
| BCL2L1 | 598 |
| BCL3 | 602 |
| BCR | 613 |
| BMPR1A | 657 |
| CALR | 811 |
| CASP1 | 834 |
| CASP2 | 835 |
| CCND2 | 894 |
| CD151 | 977 |
| CD1D | 912 |
| CD247 | 919 |
| CD3E | 916 |
| CDC42EP2 | 10435 |
| CDKN1B | 1027 |
| CDKN2C | 1031 |
| CHRNA7 | 1139 |
| CRK | 1398 |
| CTNND1 | 1500 |
| CTSD | 1509 |
| CTTN | 2017 |
| CYP19A1 | 1588 |
| DDEF1 | 50807 |
| DIO1 | 1733 |
| DOK2 | 9046 |
| DUSP2 | 1844 |
| E2F1 | 1869 |
| EGR1 | 1958 |
| EHF | 26298 |
| EPB41L2 | 2037 |
| EPHB1 | 2047 |
| EPHB6 | 2051 |
| EPS15L1 | 58513 |
| EZR | 7430 |
| FGFR3 | 2261 |
| FOS | 2353 |
| GAB1 | 2549 |
| GBP1 | 2633 |
| GNB2L1 | 10399 |
| GRB7 | 2886 |
| GSN | 2934 |
| HIC1 | 3090 |
| HOPX | 84525 |
| HSF4 | 3299 |
| HSP90B1 | 7184 |
| IGFBP3 | 3486 |
| IL24 | 11009 |
| INSRR | 3645 |
| ITGB3 | 3690 |
| KDM1A | 23028 |
| KRAS | 3845 |
| KRT16 | 3868 |
| MAP3K11 | 4296 |
| MAP4K1 | 11184 |
| MATK | 4145 |
| MCM2 | 4171 |
| MCM7 | 4176 |
| MYB | 4602 |
| NDUFA13 | 51079 |
| NFKB2 | 4791 |
| PARP1 | 142 |
| PDX1 | 3651 |

TABLE 6-continued

| GeneSymbol | EntrezGene |
|---|---|
| PGR | 5241 |
| PLAU | 5328 |
| PLAUR | 5329 |
| PLD2 | 5338 |
| PLK2 | 10769 |
| PLSCR1 | 5359 |
| POU3F4 | 5456 |
| PPIA | 5478 |
| PTP4A1 | 7803 |
| PTPN11 | 5781 |
| RAB5A | 5868 |
| RAC1 | 5879 |
| RAC2 | 5880 |
| RAF1 | 5894 |
| RALA | 5898 |
| RAP1B | 5908 |
| RGS16 | 6004 |
| RPS6KA1 | 6195 |
| RPS6KA2 | 6196 |
| RPS6KA3 | 6197 |
| RREB1 | 6239 |
| RXRA | 6256 |
| SATB1 | 6304 |
| SERPINA3 | 12 |
| SGK1 | 6446 |
| SIN3A | 25942 |
| SMAD4 | 4089 |
| SOS1 | 6654 |
| SPEN | 23013 |
| SPRR2E | 6704 |
| SRF | 6722 |
| STK3 | 6788 |
| TNFSF9 | 8744 |
| TNIP2 | 79155 |
| TUBA1A | 7846 |
| TYR | 7299 |
| WDR1 | 9948 |
| ZNF451 | 26036 |

The genes listed in Table 6 can be available from NCBI database (www.ncbi.nlm.nih.gov/) using the indicated EntrezGene number.

Also, siRNAs for inhibiting the expression of the above genes were obtained from Qiagen, and detailed matters thereof are as shown in the following Table 7 (searchable by catalog numbers contained in Qiagen homepage (http://www.qiagen.com)).

TABLE 7

| GeneSymbol | EntrezGene | Validated siRNA Catalog | |
|---|---|---|---|
| ABHD2 | 11057 | SI03140557 | SI03242806 |
| ADAM9 | 8754 | SI00056301 | SI00056308 |
| AKAP8L | 26993 | SI02622347 | SI02758987 |
| AKT2 | 208 | SI00299166 | SI00299173 |
| AMPK | 5564 | SI00086429 | SI02622242 |
| AREG | 374 | SI00299852 | SI00299936 |
| ARF5 | 381 | SI00300300 | SI03242351 |
| ARRB1 | 408 | SI02643977 | SI02776921 |
| ATP1A2 | 477 | SI00306495 | SI03054422 |
| AVIL | 10677 | SI00308476 | SI04262489 |
| BCAR3 | 8412 | SI00053102 | SI03081603 |
| BCL10 | 8915 | SI00057778 | SI03063144 |
| BCL2L1 | 598 | SI00023191 | SI03112018 |
| BCL3 | 602 | SI00073283 | SI03082156 |
| BCR | 613 | SI00288141 | SI04713422 |
| BMPR1A | 657 | SI02659622 | SI04434388 |
| CALR | 811 | SI02777096 | SI03053491 |
| CASP1 | 834 | SI02661932 | SI02662443 |
| CASP2 | 835 | SI02625546 | SI03025491 |
| CCND2 | 894 | SI00027832 | SI03071369 |
| CD151 | 977 | SI00063105 | SI02777257 |
| CD1D | 912 | SI00027916 | SI00027923 |
| CD247 | 919 | SI00014448 | SI00014462 |

TABLE 7-continued

| GeneSymbol | EntrezGene | Validated siRNA Catalog | |
|---|---|---|---|
| CD3E | 916 | SI02624230 | SI03055598 |
| CDC42EP2 | 10435 | SI00341089 | SI04348491 |
| CDKN1B | 1027 | SI02621990 | SI02621997 |
| CDKN2C | 1031 | SI00605080 | SI00605087 |
| CHRNA7 | 1139 | SI00014700 | SI03056893 |
| CRK | 1398 | SI00073780 | SI00073794 |
| CTNND1 | 1500 | SI00025382 | SI02626001 |
| CTSD | 1509 | SI00029813 | SI03097521 |
| CTTN | 2017 | SI02662485 | SI02661960 |
| CYP19A1 | 1588 | SI00002030 | SI00002044 |
| DDEF1 | 50807 | SI00360591 | SI04181800 |
| DIO1 | 1733 | SI00015764 | SI00015778 |
| DOK2 | 9046 | SI03025344 | SI03104346 |
| DUSP2 | 1844 | SI03024469 | SI04892692 |
| E2F1 | 1869 | SI00300083 | SI02664410 |
| EGR1 | 1958 | SI03052511 | SI03078950 |
| EHF | 26298 | SI04165805 | SI04283363 |
| EPB41L2 | 2037 | SI00380247 | SI04234139 |
| EPHB1 | 2047 | SI00063742 | SI02223557 |
| EPHB6 | 2051 | SI02665292 | SI02758441 |
| EPS15L1 | 58513 | SI00130403 | SI03058398 |
| EZR | 7430 | SI00302162 | SI02664228 |
| FGFR3 | 2261 | SI00002968 | SI00604772 |
| FOS | 2353 | SI00074543 | SI02781464 |
| GAB1 | 2549 | SI00031913 | SI03077403 |
| GBP1 | 2633 | SI04179595 | SI04183578 |
| GNB2L1 | 10399 | SI00084497 | SI02636662 |
| GRB7 | 2886 | SI00075607 | SI03083381 |
| GSN | 2934 | SI02664039 | SI02664046 |
| HIC1 | 3090 | SI00088970 | SI02656031 |
| HOPX | 84525 | SI03156517 | SI04323599 |
| HSF4 | 3299 | SI00442652 | SI00442659 |
| HSP90B1 | 7184 | SI02663738 | SI02655177 |
| IGFBP3 | 3486 | SI02623880 | SI02780589 |
| IL24 | 11009 | SI00092442 | SI02638139 |
| INSRR | 3645 | SI00103628 | SI00103635 |
| ITGB3 | 3690 | SI00004585 | SI02623159 |
| KDM1A | 23028 | SI00109102 | SI02781177 |
| KRAS | 3845 | SI00071015 | SI02662051 |
| KRT16 | 3868 | SI00464471 | SI00464485 |
| MAP3K11 | 4296 | SI02659552 | SI04435851 |
| MAP4K1 | 11184 | SI00095130 | SI02224257 |
| MATK | 4145 | SI00605605 | SI00605598 |
| MCM2 | 4171 | SI00064918 | SI02653525 |
| MCM7 | 4176 | SI00629104 | SI04307534 |
| MYB | 4602 | SI00076230 | SI00076237 |
| NDUFA13 | 51079 | SI00430934 | SI04249749 |
| NFKB2 | 4791 | SI00300965 | SI04224290 |
| PARP1 | 142 | SI02662989 | SI02662996 |
| PDX1 | 3651 | SI00448035 | SI04288165 |
| PGR | 5241 | SI00018690 | SI00018704 |
| PLAU | 5328 | SI02662135 | SI02662674 |
| PLAUR | 5329 | SI03033289 | SI03048458 |
| PLD2 | 5338 | SI00041244 | SI03020857 |
| PLK2 | 10769 | SI04438770 | SI04438777 |
| PLSCR1 | 5359 | SI00129332 | SI03075751 |
| POU3F4 | 5456 | SI00006748 | SI03077410 |
| PPIA | 5478 | SI00690914 | SI04351718 |
| PTP4A1 | 7803 | SI00052213 | SI03065118 |
| PTPN11 | 5781 | SI00044002 | SI02225909 |
| RAB5A | 5868 | SI02655037 | SI02632602 |
| RAC1 | 5879 | SI03065531 | SI02655051 |
| RAC2 | 5880 | SI00044947 | SI02655058 |
| RAF1 | 5894 | SI00301623 | SI02223032 |
| RALA | 5898 | SI00076594 | SI02662835 |
| RAP1B | 5908 | SI00111769 | SI02662303 |
| RGS16 | 6004 | SI03063760 | SI03069178 |
| RPS6KA1 | 6195 | SI02223060 | SI02223067 |
| RPS6KA2 | 6196 | SI02225006 | SI04379487 |
| RPS6KA3 | 6197 | SI00288190 | SI00288197 |
| RREB1 | 6239 | SI03195605 | SI04264995 |
| RXRA | 6256 | SI00046130 | SI00046144 |
| SATB1 | 6304 | SI00046298 | SI00046319 |
| SERPINA3 | 12 | SI00715519 | SI00715526 |
| SGK1 | 6446 | SI00079688 | SI00287798 |
| SIN3A | 25942 | SI00719068 | SI02781240 |
| SMAD4 | 4089 | SI00076020 | SI00076041 |
| SOS1 | 6654 | SI00079793 | SI00079807 |
| SPEN | 23013 | SI03077697 | SI02641128 |
| SPRR2E | 6704 | SI02821574 | SI02821588 |
| SRF | 6722 | SI02757622 | SI03034731 |
| STK3 | 6788 | SI02622256 | SI02622263 |
| TNFSF9 | 8744 | SI03036684 | SI03096576 |
| TNIP2 | 79155 | SI00748769 | SI04174037 |
| TUBA1A | 7846 | SI00753298 | SI00753305 |
| TYR | 7299 | SI04255055 | SI04308136 |
| WDR1 | 9948 | SI00761712 | SI03122448 |
| ZNF451 | 26036 | SI04152232 | SI04237191 |

The siRNAs against the targets can be available from Qiagen homepage (http://www.qiagen.com) using the indicated catalog numbers.

Example 2

Measurement of Anti-c-Met Antibody Efficacy Change According to Expression Suppression of 111 Candidate Genes in a Variety of Cell Lines To see what influences the genes obtained above have on the efficacy of an anti-c-Met antibody in other cell lines besides the MKN45 gastric cancer cell line, synthetic lethal screening was conducted in cell lines other than the MKN45 gastric cancer cell line using 111 genes chosen in Example 1. The cell lines used are BxPC-3 pancreatic cancer cell line (ATCC, CRL-1687), HCC827 lung cancer cell line (ATCC, CRL-2868), HCC1954 breast cancer cell line (ATCC, CRL-2338), NCI-N87 gastric cancer cell line (ATCC, CRL-5822), and RKO colorectal cancer cell line (ATCC, CRL-2577).

A small library consisting of a mixture of 2 siRNAs was used for each gene of the above 111 genes, and Example 1 was consulted for this experiment. The experiment was also conducted with regard to the MKN45 cell line at the same time. The thus obtained SI values are shown in Table 8, and a hitmap regarding the SI values is shown in FIG. 1.

TABLE 8

SI values of Chosen 111 Genes in a Variety of Cell Lines

| GeneSymbol | BxPC-3 | HCC827 | HCC1954 | NCI-N87 | RKO | MKN45 |
|---|---|---|---|---|---|---|
| RAF1 | 0.9938459 | 0.9252506 | 0.770076 | 1.0003722 | 0.9681162 | 0.4780411 |
| PARP1 | 0.8319921 | 0.6642204 | 0.8384414 | 0.7338909 | 0.7992572 | 0.4968378 |
| CALR | 0.8999902 | 0.6448412 | 0.6982548 | 1.1195109 | 1.2190372 | 0.5045961 |
| PLAUR | 0.9899638 | 0.9424982 | 0.7989792 | 0.6659523 | 0.9003028 | 0.5089088 |
| BCL2L1 | 0.94435 | 0.7677864 | 0.6359504 | 0.651353 | 0.9247476 | 0.5234986 |
| SIN3A | 1.0579296 | 0.948844 | 1.0241834 | 0.9764304 | 0.9158921 | 0.5245741 |
| CRK | 0.9916592 | 0.5902896 | 0.7025079 | 1.0116105 | 1.0766968 | 0.5290723 |
| DOK2 | 1.0644807 | 1.0299056 | 1.9615747 | 1.0818866 | 0.9461325 | 0.5293834 |
| SRF | 0.8319116 | 0.9355485 | 0.8234819 | 1.3324415 | 0.9604646 | 0.5571768 |

TABLE 8-continued

SI values of Chosen 111 Genes in a Variety of Cell Lines

| GeneSymbol | BxPC-3 | HCC827 | HCC1954 | NCI-N87 | RKO | MKN45 |
|---|---|---|---|---|---|---|
| AKT2 | 1.0482393 | 0.6938421 | 0.480413 | 0.6881763 | 1.0134572 | 0.5590485 |
| AMPK | 1.3750395 | 1.0435904 | 0.8855621 | 0.8723191 | 0.9252578 | 0.5622495 |
| SGK1 | 0.9712563 | 1.0372907 | 0.7942785 | 0.9572418 | 0.9771521 | 0.5678264 |
| RAC2 | 0.9516706 | 0.913748 | 0.7663909 | 0.9286388 | 0.9626119 | 0.5685923 |
| DIO1 | 0.9339036 | 0.8705356 | 0.8564505 | 1.008191 | 0.9622485 | 0.5730143 |
| HSP90B1 | 1.0598936 | 1.0800234 | 1.3544266 | 1.1868872 | 0.9245217 | 0.57518 |
| EPS15L1 | 1.0397547 | 1.0065742 | 1.6663654 | 1.1788162 | 0.963267 | 0.578936 |
| RGS16 | 1.1463116 | 1.1251288 | 1.2682568 | 1.1688809 | 0.9037466 | 0.5796951 |
| PLSCR1 | 1.0009141 | 0.9505103 | 0.6492171 | 0.7662584 | 0.8776844 | 0.5816549 |
| BMPR1A | 0.9871944 | 0.9322132 | 0.95591 | 1.114344 | 0.9985085 | 0.5969066 |
| SOS1 | 0.9573801 | 1.1280254 | 0.7275482 | 1.0309629 | 0.9974581 | 0.5992077 |
| ZNF451 | 1.0770473 | 1.015884 | 1.2375149 | 0.9270675 | 0.9201858 | 0.6008823 |
| GRB7 | 0.8221604 | 0.9679874 | 1.0445158 | 0.9521513 | 0.9148365 | 0.6069551 |
| WDR1 | 1.048445 | 1.351535 | 1.5014853 | 1.0627326 | 0.877683 | 0.6086867 |
| TNIP2 | 1.4186503 | 1.1658437 | 1.6366343 | 1.28343 | 0.919652 | 0.6111594 |
| ITGB3 | 0.6609622 | 0.8452912 | 0.5603533 | 1.0084644 | 1.0982376 | 0.6178068 |
| KRT16 | 1.0472548 | 0.9361049 | 1.0082653 | 1.1288111 | 0.9145986 | 0.6182366 |
| FGFR3 | 0.6646828 | 0.5182343 | 0.9676631 | 1.0605242 | 1.0351426 | 0.6203211 |
| KRAS | 0.8367682 | 0.8866842 | 0.9499789 | 1.1934058 | 0.8855654 | 0.6212177 |
| CTTN | 0.987187 | 0.6464489 | 0.800683 | 1.0412639 | 1.0074744 | 0.6226066 |
| PLAU | 0.9454672 | 1.0245278 | 1.0458566 | 0.6861733 | 0.9197069 | 0.6244581 |
| CTSD | 0.9868983 | 0.6280849 | 0.5562315 | 1.1041565 | 0.9522809 | 0.626109 |
| CDC42EP2 | 0.9220212 | 0.946319 | 1.0072959 | 0.9703077 | 0.9673717 | 0.6317562 |
| CD1D | 0.8893234 | 1.0449331 | 0.763342 | 1.2039545 | 1.2026623 | 0.632607 |
| RPS6KA1 | 0.952036 | 0.7745923 | 0.9042757 | 1.2891912 | 1.0011318 | 0.6378934 |
| GNB2L1 | 0.974204 | 0.9176814 | 0.8765843 | 0.9700562 | 0.995209 | 0.6392188 |
| SATB1 | 0.9612086 | 0.93517 | 0.8930937 | 0.8780781 | 0.9469096 | 0.6410084 |
| CDKN2C | 0.7855692 | 0.7719736 | 0.897036 | 1.208338 | 0.9801459 | 0.6416255 |
| TNFSF9 | 0.9291001 | 0.9666466 | 0.8321276 | 1.143697 | 0.956764 | 0.642139 |
| INSRR | 0.9286198 | 0.7382155 | 0.8142393 | 1.0226883 | 1.2387707 | 0.6430102 |
| RAC1 | 1.0123408 | 1.2834318 | 1.0279699 | 0.7251248 | 1.0055349 | 0.6430277 |
| SPEN | 0.9842789 | 1.2259665 | 1.3179302 | 1.2414549 | 0.8765679 | 0.6441563 |
| RPS6KA2 | 1.049877 | 1.1472913 | 1.5065256 | 1.1252971 | 0.9434615 | 0.6443193 |
| CASP1 | 0.9550224 | 0.3612137 | 0.5551167 | 1.2022877 | 1.0128297 | 0.645677 |
| CD151 | 0.8456032 | 0.7932733 | 0.5685474 | 1.0346555 | 1.2921733 | 0.6492715 |
| PLD2 | 1.0987017 | 1.0643933 | 0.7469183 | 0.7127279 | 0.9000124 | 0.6502977 |
| RAB5A | 1.0548745 | 1.0785055 | 1.1624358 | 0.8878197 | 0.88085 | 0.6532652 |
| MYB | 1.0768883 | 1.185848 | 0.8998033 | 1.0298121 | 0.9917325 | 0.6558677 |
| BCR | 1.0253089 | 0.8303693 | 0.6835704 | 0.8117236 | 1.3113774 | 0.6574621 |
| RXRA | 1.0245594 | 0.9252511 | 0.9640817 | 0.9839192 | 0.9320988 | 0.6576106 |
| MAP3K11 | 0.9716306 | 0.9421711 | 0.9227024 | 1.0063672 | 1.1482072 | 0.6586961 |
| CASP2 | 0.7928462 | 0.9745779 | 0.4883288 | 1.0991855 | 0.9252272 | 0.6603077 |
| EZR | 1.0405666 | 1.0347886 | 1.0047234 | 0.991052 | 1.0077985 | 0.6610253 |
| SPRR2E | 0.8713719 | 1.0517796 | 0.7398009 | 1.2051403 | 0.9293335 | 0.6627782 |
| IGFBP3 | 0.6773173 | 0.736601 | 0.7194122 | 1.026766 | 1.0502694 | 0.6636266 |
| SERPINA3 | 1.0289106 | 1.067729 | 0.7598079 | 0.7241833 | 0.868831 | 0.6650286 |
| PPIA | 0.9473245 | 0.8664254 | 0.9231841 | 0.7477531 | 0.8474461 | 0.6663135 |
| HIC1 | 0.9093966 | 0.7932718 | 0.9873954 | 0.9974532 | 0.9546506 | 0.6677616 |
| PLK2 | 0.9904952 | 0.8796158 | 2.123309 | 1.1564023 | 1.0000087 | 0.6696779 |
| IL24 | 1.0154534 | 0.8043648 | 1.3177825 | 1.2373697 | 1.0007712 | 0.6705811 |
| RALA | 0.998575 | 0.9401821 | 0.861517 | 0.9995303 | 0.9718574 | 0.6745642 |
| TUBA1A | 1.0800985 | 0.8599321 | 1.1314882 | 0.9962044 | 0.9899493 | 0.6766664 |
| BCL3 | 0.8713893 | 0.8592477 | 0.5541921 | 0.7058519 | 1.0278773 | 0.6818978 |
| EPHB1 | 0.8627981 | 0.7887248 | 0.8844306 | 0.9594339 | 0.9680765 | 0.6840304 |
| HOPX | 1.0285287 | 1.0653046 | 2.2915811 | 1.0911851 | 0.9430435 | 0.6858705 |
| KDM1A | 0.9812326 | 1.2088877 | 2.0420855 | 1.1051456 | 0.904733 | 0.6878664 |
| CHRNA7 | 1.0989291 | 0.6878248 | 0.8295477 | 1.0214985 | 0.9500896 | 0.6914161 |
| PTP4A1 | 1.1037251 | 0.769887 | 0.842557 | 0.9528268 | 0.9758464 | 0.6918624 |
| CYP19A1 | 0.7770703 | 0.6607876 | 0.6521505 | 1.1013243 | 0.9133785 | 0.6988482 |
| DDEF1 | 1.1095569 | 0.9954366 | 1.1413488 | 1.1494222 | 0.8738631 | 0.6994487 |
| STK3 | 0.9014655 | 0.9317094 | 1.118511 | 1.2433596 | 0.9099637 | 0.7021648 |
| NDUFA13 | 1.0900881 | 0.9556917 | 1.8428588 | 1.1156596 | 0.9452809 | 0.7024794 |
| AVIL | 1.1307899 | 0.5708994 | 1.3554068 | 1.0571651 | 0.9364259 | 0.7036659 |
| CD3E | 0.8658876 | 0.9090761 | 0.4077484 | 1.0569019 | 1.0929389 | 0.7054417 |
| AREG | 0.8719837 | 0.7478221 | 0.7815538 | 0.6703939 | 0.8172028 | 0.7061657 |
| NFKB2 | 1.0043727 | 1.2471616 | 0.8383249 | 1.0525012 | 1.0056007 | 0.7083075 |
| CD247 | 0.8393396 | 0.6749429 | 0.7235493 | 1.0651329 | 1.0162503 | 0.7127282 |
| GAB1 | 0.7684962 | 0.9540878 | 0.9377277 | 1.0217521 | 1.05686 | 0.7193563 |
| PDX1 | 0.8351508 | 0.968195 | 0.9769631 | 0.9788405 | 1.1898872 | 0.7236283 |
| CDKN1B | 0.9409836 | 0.9897178 | 0.9656333 | 1.1199602 | 0.9181031 | 0.7244534 |
| MATK | 1.0170145 | 1.0072675 | 0.9203868 | 0.9672675 | 0.9430117 | 0.7264676 |
| ATP1A2 | 0.9366922 | 0.6917147 | 0.8200824 | 0.6011073 | 0.9909109 | 0.726556 |
| MCM2 | 0.9793229 | 0.9373572 | 0.9373792 | 0.9714727 | 1.0537148 | 0.7282562 |
| EGR1 | 0.9085595 | 0.9105525 | 0.8788532 | 1.0034482 | 1.1147494 | 0.7299723 |
| RAP1B | 1.6268314 | 1.0067436 | 1.1826498 | 1.0372141 | 0.9435485 | 0.7312763 |
| MCM7 | 0.9745641 | 1.0112594 | 0.7826385 | 0.950741 | 1.005545 | 0.7382996 |

TABLE 8-continued

SI values of Chosen 111 Genes in a Variety of Cell Lines

| GeneSymbol | BxPC-3 | HCC827 | HCC1954 | NCI-N87 | RKO | MKN45 |
|---|---|---|---|---|---|---|
| E2F1 | 0.9149797 | 0.8015904 | 0.9741151 | 1.0210524 | 0.9494526 | 0.7433683 |
| ADAM9 | 1.1833961 | 1.1021414 | 1.2695076 | 1.2550234 | 1.0496721 | 0.7555447 |
| TYR | 0.9944545 | 1.200577 | 1.4590544 | 1.2314105 | 1.0302137 | 0.7595515 |
| HSF4 | 1.1626691 | 0.8571481 | 0.7961518 | 0.9673071 | 0.9398134 | 0.7597731 |
| MAP4K1 | 0.9853304 | 1.117042 | 1.9456093 | 1.06136 | 1.0382221 | 0.7628011 |
| BCAR3 | 0.8758348 | 0.1165817 | 0.98824 | 1.1946684 | 0.9390212 | 0.7710775 |
| PTPN11 | 1.0784 | 1.2210339 | 0.8718976 | 0.7376827 | 0.9431712 | 0.7824097 |
| CTNND1 | 0.8650683 | 0.5282904 | 0.5704443 | 1.0751567 | 0.9623115 | 0.7898436 |
| RPS6KA3 | 1.0679356 | 1.207054 | 1.2248074 | 1.3868566 | 0.949868 | 0.795511 |
| ARRB1 | 1.0003328 | 0.9065651 | 0.7078428 | 0.6305473 | 1.0333544 | 0.7994589 |
| CCND2 | 0.9551436 | 0.7531394 | 0.5088614 | 1.1499292 | 1.1501382 | 0.813013 |
| AKAP8L | 1.0867205 | 0.7860187 | 1.2597878 | 1.1782427 | 0.8839827 | 0.8171114 |
| FOS | 0.8296408 | 0.848979 | 0.795645 | 1.0745124 | 1.4058896 | 0.8171838 |
| EPB41L2 | 0.9337943 | 0.7753879 | 0.742665 | 0.9830314 | 0.9475393 | 0.824284 |
| GBP1 | 0.9610536 | 0.8763407 | 0.9212894 | 0.9974391 | 0.928348 | 0.8272798 |
| DUSP2 | 0.9481382 | 0.9781033 | 0.8040963 | 0.9308642 | 1.2586017 | 0.8409697 |
| POU3F4 | 0.9911525 | 0.9512652 | 0.6243071 | 0.8383849 | 0.888373 | 0.8431052 |
| BCL10 | 1.0303372 | 1.0304834 | 1.3897274 | 1.3539582 | 0.8876128 | 0.845582 |
| GSN | 0.9989689 | 0.6317692 | 0.9488322 | 0.9121666 | 0.9366791 | 0.8512136 |
| EHF | 1.0016998 | 0.7628551 | 1.2517028 | 0.9205452 | 0.93207 | 0.8723551 |
| RREB1 | 0.9885682 | 1.221822 | 1.0155602 | 1.0853222 | 1.0182388 | 0.8796528 |
| ABHD2 | 1.0106019 | 0.7732307 | 1.465196 | 1.4227781 | 0.9271693 | 0.8815108 |
| ARF5 | 0.9564934 | 0.7311287 | 0.7167929 | 0.7042404 | 1.054821 | 0.8981253 |
| SMAD4 | 0.9738075 | 1.0410381 | 0.8473416 | 1.0218506 | 1.0195587 | 0.9162142 |
| EPHB6 | 1.0750516 | 0.5891416 | 0.7981435 | 0.9667099 | 0.8805723 | 0.9243932 |
| PGR | 0.9818549 | 1.1072992 | 0.9187917 | 0.91141 | 1.016999 | 1.1150011 |

Example 3

Measurement of Cancer Cell Growth Suppression by Combination Administration of FGFR3 siRNA and Anti-c-Met Antibody To see whether the expression suppression of FGFR3 among the genes chosen in Example 1 increases the efficacy of an anti-c-Met antibody, the effects of the combination administration of FGFR3 siRNA and anti-c-Met antibody were examined in a variety of cell lines.

3.1. Effects in MKN45 Gastric Cancer Cell Line

First, tests were carried out using MKN45 gastric cancer cell line in which the screening of the gene was conducted. As a control group, All Negative control siRNA (Qiagen, cat. no. 1027281) was used, and as a target siRNA, a mixture of two kinds of siRNAs (see Table 7) that had effects during the screening was used. 0.3 ul of RNAiMax diluted in Opti-MEM and an siRNA mixture with a final concentration of 20~40 nm were mixed in a 96-well plate, which was incubated at a room temperature for 15 min. A total volume of the diluted RNAiMax and siRNA was adjusted to be 25 ul. 80 ul of cells diluted in a 10% (v/v) FBS-containing RPMI1640 medium (GIBCO) were seeded onto each well of the 96-well plate so that each well contained 5000 cells. After 24 hours, the cultured cells were treated with L3-1Y/IgG2 antibody prepared in Reference Example 1 at a concentration of 0.016 ug/ml.

72 hours later after the treatment, 100 uL of CellTiter Glo solution (Promega, G7572) was added to each well, which was allowed to stay at a room temperature for 30 min. The number of cells was counted via luminescence signals, which were recorded using Envision 2104 Multi-label Reader (Perkin Elmer). For the measurement of apoptosis level, 100 ul of Caspase-3/7 Glo solution (Promega, G8092) was added to each well of another 96-well plate, which was allowed to stay at a room temperature for 30 min. The number of cells was counted via luminescence signals, which were recorded using Envision 2104 Multi-label Reader (Perkin Elmer).

Figure 2:
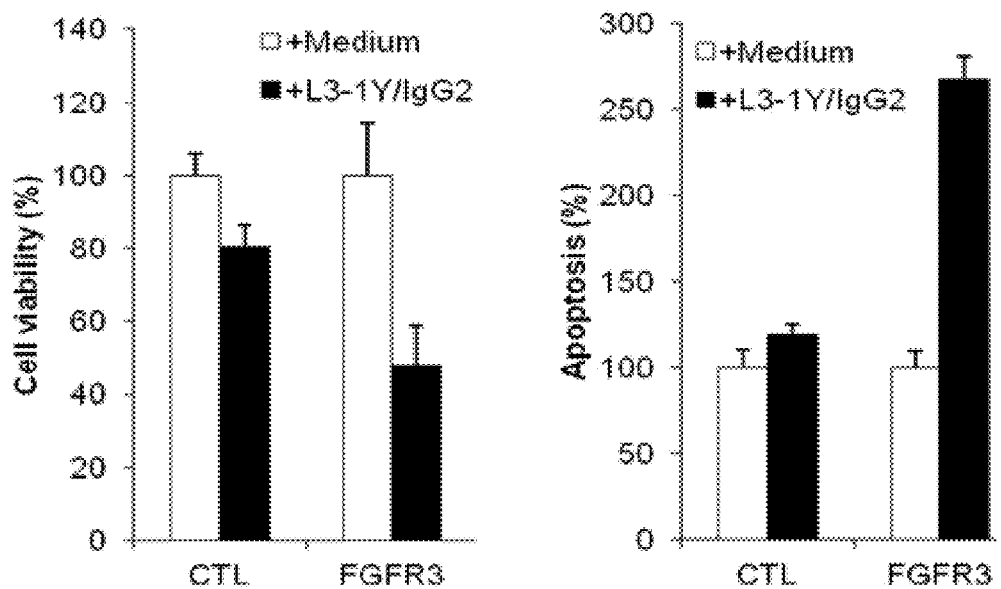
FIG. 2 is a graph showing cell viability (left) and apoptosis (right) after co-administration of FGFR3 siRNA and L3-1Y/IgG2 antibody to a MKN45 gastric cancer cell line.

The thus obtained results (cell viability and apoptosis results) are shown in FIG. 2. As seen in FIG. 2, when FGFR3 siRNA was treated, the cancer cell growth inhibitory efficacy of the L3-1Y/IgG2 antibody was increased in comparison with the control. Also, apoptosis was remarkably increased and from this, it can be concluded that the suppression of FGFR3 expression causes apoptosis to increase the efficacy of the L3-1Y/IgG2 antibody.

3.2. Effects in HT29 Colorectal Cancer Cell Line

The efficacy of the combination administration of FGFR3 siRNA and L3-1Y/IgG2 antibody was examined in a colorectal cancer cell line on which the anti-c-Met antibody has no effects. For this, HT29 (ATCC, HTB-38) cells were used. As a control group, All Negative control siRNA (Qiagen, cat. no. 1027281) was used, and as a target siRNA, a mixture of two kinds of siRNAs (see Table 7) that had effects during the screening was used. Transfection was carried out by the same procedures as Example 3.1 and after 24 hours, the cultured cells were treated with L3-1Y/IgG2 antibody at 0 ug/ml, 0.016 ug/ml, 0.08 ug/ml, 0.4 ug/ml, and 2 ug/ml, respectively.

72 hours later after the treatment, 100 uL of CellTiter Glo solution (Promega, G7572) was added to each well, which was allowed to stay at a room temperature for 30 min. The number of cells was counted via luminescence signals, which were recorded using Envision 2104 Multi-label Reader (Perkin Elmer).

Figure 3:
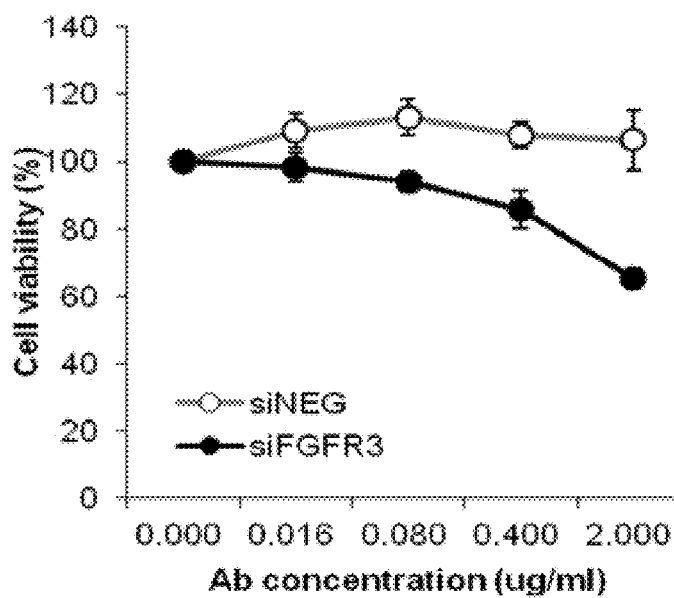
FIG. 3 is a graph showing cell viability of HT29 colorectal cancer cells co-treated with FGFR3 siRNA and L3-1Y/IgG2 antibody, wherein "siNEG" refers to a negative control siRNA (Qiagen, cat. no. 1027281).

The thus obtained result (cell viability) is shown in FIG. 3. As in FIG. 3, when the L3-1Y/IgG2 antibody and FGFR3 siRNA were co-treated, cancer cell growth inhibitory efficacy which did not occur when treated with the L3-1Y/IgG2 antibody alone was exhibited, and this result is to show synergistic effects by the combination administration of FGFR3 siRNA and L3-1Y/IgG2 antibody in HT-29 cells.

Example 4

Measurement of Cancer Cell Growth Suppression by Combination Administration of RAF1 siRNA and Anti-c-Met Antibody

To see whether the expression suppression of RAF1 among the genes chosen in Example 1 increases the efficacy of an anti-c-Met antibody, the effects of the combination administration of RAF1 siRNA and anti-c-Met antibody were examined in a variety of cell lines.

4.1. Effects in MKN45 Gastric Cancer Cell Line

First, tests were carried out using MKN45 gastric cancer cell line in which the screening of the gene was conducted. As a control group, All Negative control siRNA (Qiagen, cat. no. 1027281) was used, and as a target siRNA, a mixture of two kinds of siRNAs (see Table 7) that had effects during the screening was used. Transfection was carried out by the same procedures as Example 3.1 and after 24 hours, the cultured cells were treated with L3-1Y/IgG2 antibody in amounts of 0 ug/ml, 0.016 ug/ml, 0.08 ug/ml, 0.4 ug/ml, or 2 ug/ml. 72 hours later after the treatment, 100 uL of CellTiter Glo solution (Promega, G7572) was added to each well, which was allowed to stay at a room temperature for 30 min. The number of cells was counted via luminescence signals, which were recorded using Envision 2104 Multi-label Reader (Perkin Elmer).

Figure 4:
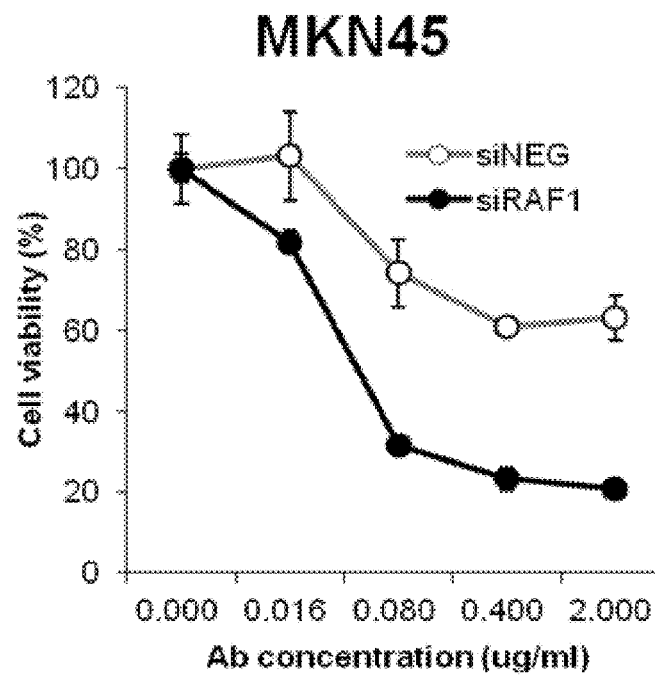
FIG. 4 is a graph showing cell viability of MKN45 gastric cancer cells co-treated with RAF1 siRNA and L3-1Y/IgG2 antibody.

The thus obtained result is shown in FIG. 4. As in FIG. 4, when the L3-1Y/IgG2 antibody and RAF1 siRNA were co-treated, the efficacy of the L3-1Y/IgG2 antibody was remarkably increased, and this is to show that synergistic effects by the combination administration of RAF1 siRNA and L3-1Y/IgG2 antibody in MKN45 cells occurred.

4.2. Effects in EBC1 Lung Cancer Cell Line

The efficacy of the combination administration of RAF1 siRNA and L3-1Y/IgG2 antibody was examined in lung cancer cell line on which the anti-c-Met antibody has an effect. For this, EBC1 (JCRB, JCRB0820) cells were used. As a control group, All Negative control siRNA (Qiagen, cat. no. 1027281) was used, and as a target siRNA, a mixture of two kinds of siRNAs (see Table 7) that had effects during the screening was used. Transfection was carried out by the same procedures as Example 3.1 and after 24 hours, the cultured cells were treated with L3-1Y/IgG2 antibody at 0 ug/ml, 0.016 ug/ml, 0.08 ug/ml, 0.4 ug/ml, or 2 ug/ml. After 5 days of treatment, for cell number counting, 20 ul of a diluting solution of CellTiter Blue (Promega, G8081) and HBSS at 1:1 was added to each well, which was incubated at 37° C. for 4 hours. Then, the number of cells was counted via fluorescence signals (560/590 nm), which were measured using Envision 2104 Multi-label Reader (Perkin Elmer).

Figure 5:
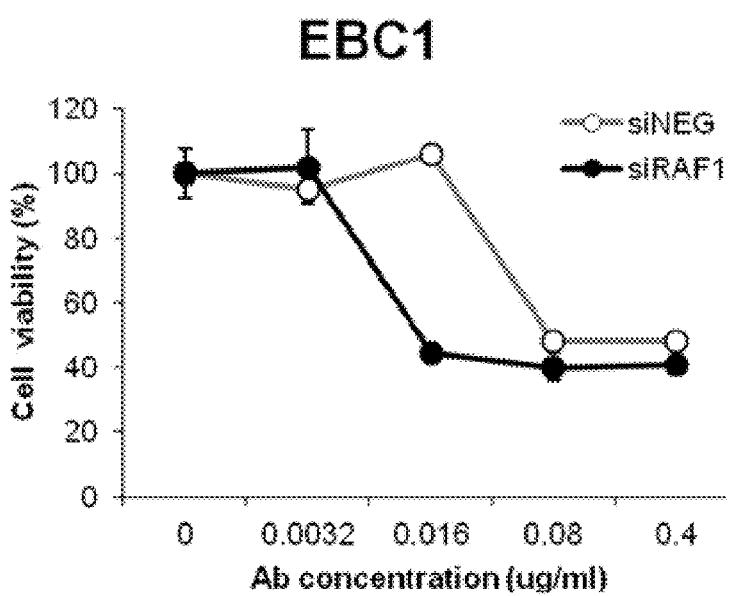
FIG. 5 is a graph showing cell viability of EBC1 lung cancer cells co-treated with RAF1 siRNA and L3-1Y/IgG2.

The thus obtained result is shown in FIG. 5. As in FIG. 5, when the L3-1Y/IgG2 antibody and RAF1 siRNA were co-treated, a concentration at which the L3-1Y/IgG2 antibody showed the maximized efficacy was decreased to 0.016 ug/ml from 0.08 ug/ml by ⅕.

4.3. Effects in Resistance-Acquired Cell Line Against L3-1Y/IgG2 Antibody

To see whether the treatment RAF1 siRNA can overcome resistance acquired due to the repetitive treatment of an antibody, tests were carried out using MKN45 gastric cancer cell line which had been treated by L3-1Y/IgG2 antibody for 3 months or longer and acquired resistance against it. The resistance-acquired MKN45 gastric cancer cell line was prepared as follows: MKN45 cells (JCRB, JCRB0254) were treated with L3-1Y/IgG2 antibody in amounts being increased over 3 months or longer. The amount of L3-1Y/IgG2 antibody to be treated started from its initial treatment concentration of 1 ug/ml and was increased up to 10 ug/ml until resistance occurred. To confirm the acquisition of L3-1Y/IgG2 antibody resistance, the resistance-acquired clones were treated or not treated with L3-1Y/IgG2 antibody and then incubated, followed by CTG assays.

Figure 6:
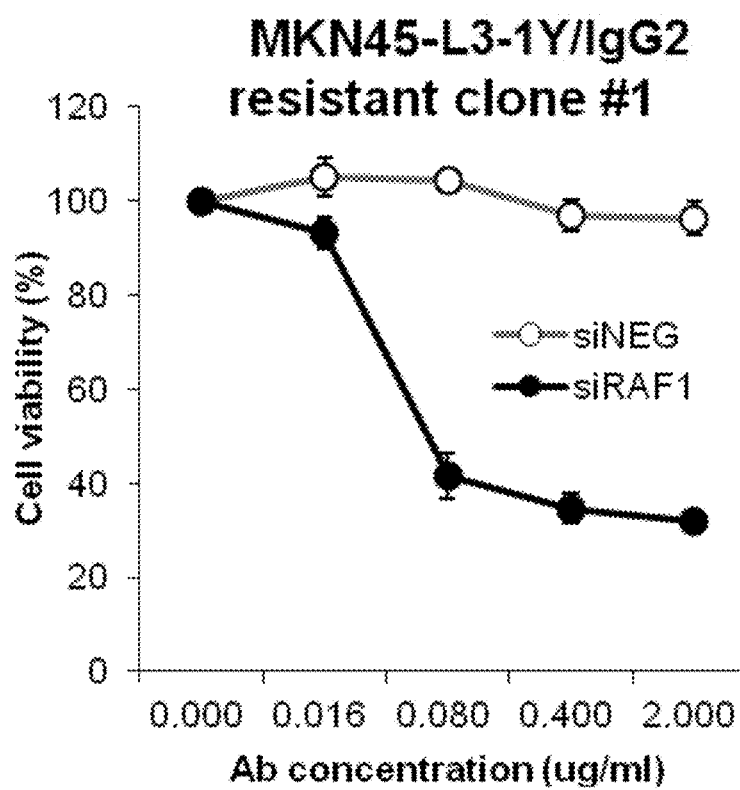
FIG. 6 is a graph showing cell viability of MKN45 gastric cancer cells having an acquired resistance against L3-1Y/IgG2 antibody co-treated with RAF1 siRNA and L3-1Y/IgG2 antibody.

As a control group, All Negative control siRNA (Qiagen, cat. no. 1027281) was used, and as a target siRNA, a mixture of two kinds of siRNAs (see Table 7) that had effects during the screening was used. Tests were carried out by the same procedures as Example 4.1 and the obtained result is shown in FIG. 6. As in FIG. 6, when the L3-1Y/IgG2 antibody and RAF1 siRNA were co-treated, cancer cell growth inhibitory efficacy which did not occur when treated with the L3-1Y/IgG2 antibody alone was exhibited. This suggests that the acquired resistance of the anti-c-Met antibody can be overcome through the suppression of RAF1.

Example 5

Measurement of Cancer Cell Growth Suppression by Combination Administration of ITGB3 siRNA and Anti-c-Met Antibody

To see whether the expression suppression of ITGB3 among the genes chosen in Example 1 increases the efficacy of an anti-c-Met antibody, the effects of the combination administration of ITGB3 siRNA and anti-c-Met antibody were first examined in MKN45 gastric cancer cell line.

5.1. Effects in MKN45 Gastric Cancer Cell Line

First, tests were carried out using MKN45 gastric cancer cell line in which the screening of the gene was conducted. As a control group, All Negative control siRNA (Qiagen, cat. no. 1027281) was used (indicated as siNEG), and as a target siRNA, a mixture of two kinds of siRNAs (see Table 7) that had effects during the screening was used. Transfection was carried out by the same procedures as Example 3.1 and after 24 hours, the cultured cells were treated with L3-1Y/IgG2 antibody at 0 ug/ml, 0.016 ug/ml, 0.08 ug/ml, 0.4 ug/ml, or 2 ug/ml. 72 hours later after the treatment, 100 uL of CellTiter Glo solution (Promega, G7572) was added to each well, which was allowed to stay at a room temperature for 30 min. The number of cells was counted via luminescence signals, which were recorded using Envision 2104 Multi-label Reader (Perkin Elmer).

Figure 7:
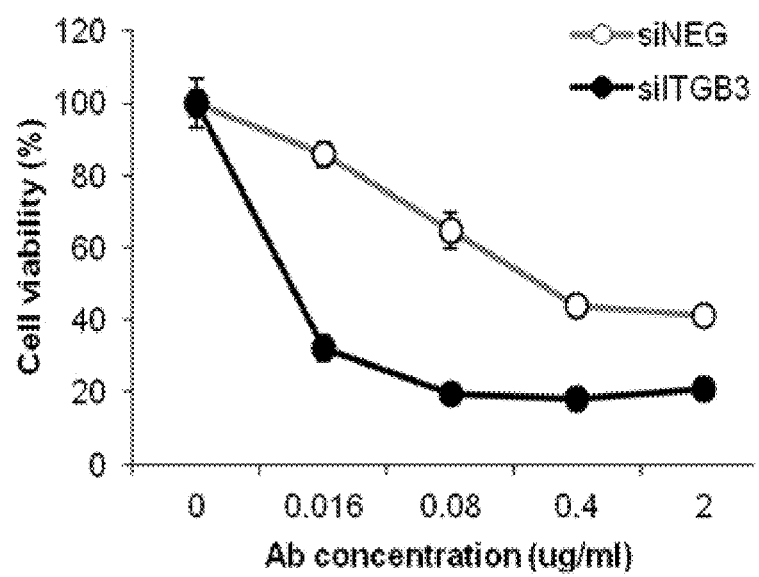
FIG. 7 is a graph showing cell viability of MKN45 gastric cancer cells co-treated with ITGB3 siRNA and L3-1Y/IgG2 antibody.

The thus obtained result is shown in FIG. 7. As in FIG. 7, when the L3-1Y/IgG2 antibody and ITGB3 siRNA were co-treated, the efficacy of the L3-1Y/IgG2 antibody was remarkably increased, and this is to show that synergistic effects by the combination administration of ITGB3 siRNA and L3-1Y/IgG2 antibody in MKN45 cells occurred.

5.2. Effects in Breast Cancer Cell Line

The efficacy of the combination administration of ITGB3 siRNA and L3-1Y/IgG2 antibody was examined in a breast cancer cell line on which the anti-c-Met antibody alone has no effects. For this, HCC1806 (ATCC, CRL-2335) and HCC1954 (ATCC, CRL-2338) cells were used.

As a control group, All Negative control siRNA (Qiagen, cat. no. 1027281) was used, and as a target siRNA, a mixture of two kinds of siRNAs (see Table 7) that had effects during the screening was used. Transfection was carried out by the same procedures as Example 3.1 and after 24 hours, the cultured cells were treated with L3-1Y/IgG2 antibody at 0 ug/ml, 0.016 ug/ml, 0.08 ug/ml, 0.4 ug/ml, or 2 ug/ml. 72 hours later after the treatment, 100 uL of CellTiter Glo solution (Promega, G7572) was added to each well, which was allowed to stay at a room temperature for 30 min. The number of cells was counted via luminescence signals, which were recorded using Envision 2104 Multi-label Reader (Perkin Elmer).

Figure 8A:
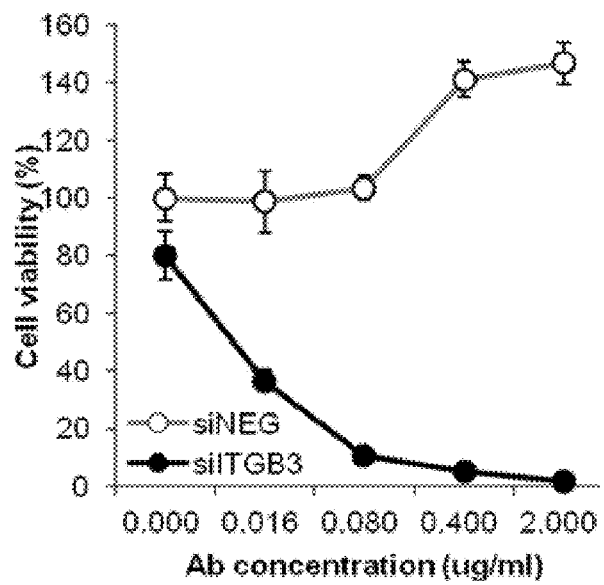
FIG. 8A is a graph showing cell viability of HCC1806 cells co-treated with ITGB3 siRNA and L3-1Y/IgG2 antibody.
Figure 8B:
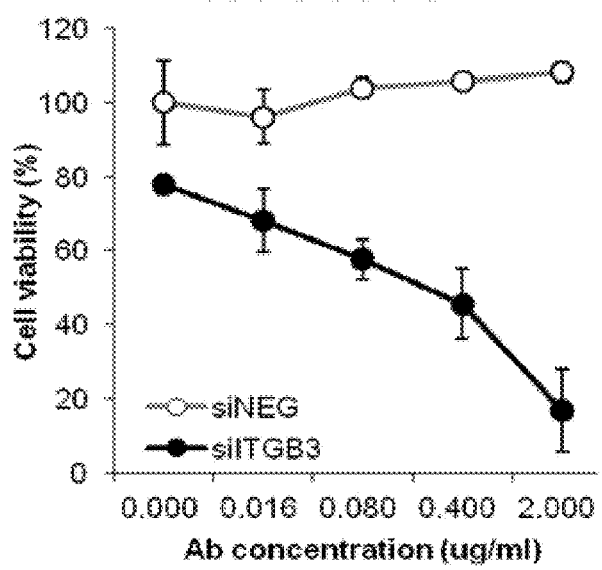
FIG. 8B is a graph showing cell viability of HCC1954 cells co-treated with ITGB3 siRNA and L3-1Y/IgG2 antibody.

The thus obtained result is shown in FIG. 8. As in FIG. 8, when the L3-1Y/IgG2 antibody and ITGB3 siRNA were co-treated, cancer cell growth inhibitory efficacy which did not occur when treated with the L3-1Y/IgG2 antibody alone was strongly exhibited in both of two kinds of breast cancer cell lines, and this is to show synergistic effects by the combination administration of ITGB3 siRNA and L3-1Y/IgG2 antibody in these breast cancer cell lines.

5.3. Effects in Resistance-Acquired Cell Line Against L3-1Y/IgG2 Antibody

To verify whether the treatment with ITGB3 siRNA can overcome resistance acquired due to the repetitive treatment of an antibody, tests were carried out using MKN45 gastric cancer cell line (see Example 4.3) which had been treated by L3-1Y/IgG2 antibody for 3 months or longer and acquired resistance against it.

Figure 9:
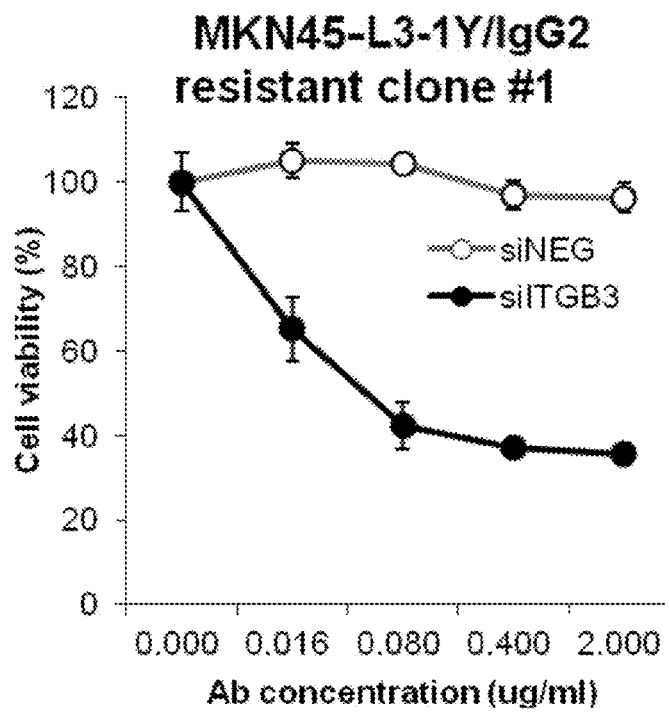
FIG. 9 is a graph showing cell viability of MKN45 gastric cancer cells having an acquired resistance against L3-1Y/IgG2 antibody co-treated with ITGB3 siRNA and L3-1Y/IgG2 antibody.

As a control group, All Negative control siRNA (Qiagen, cat. no. 1027281) was used, and as a target siRNA, a mixture of two kinds of siRNAs (see Table 7) that had effects during the screening was used. Tests were carried out by the same procedures as the MKN45 experiment of Example 5.1 and the obtained result is shown in FIG. 9. As shown in FIG. 9, when the L3-1Y/IgG2 antibody and ITGB3 siRNA were co-treated, cancer cell growth inhibitory efficacy which did not occur when treated with the L3-1Y/IgG2 antibody alone was exhibited, and this suggests that the acquired resistance of the anti-c-Met antibody can be overcome through the suppression of ITGB3.

Example 6

Cancer Cell Growth Inhibition by Co-Administration of BCL2L1 siRNA and Anti-c-Met Antibody To verify whether the suppression of the expression of BCL2L1 among the selected genes in Example 1 can lead to increase in the efficacy of anti-c-Met antibody, the effect of co-administration of BCL2L1 siRNA and an anti-c-Met antibody was examined in MKN45 gastric cancer cells.

As a control, all negative control siRNA (Qiagen, cat. no. 1027281) was used, and as a target siRNA, a mixture of two kinds of siRNAs (see Table 7) that exhibit effects during the screening was used. 0.3 ul RNAiMax, which is diluted with Opti-MEM, and siRNA mixture at the final concentration of 20~40 nM were mixed in 96 well plate, and incubated at room temperature for 15 minutes. The final total volume of the mixture of the diluted RNAiMax and siRNA was 25 ul. 80 ul of cells, which were diluted with RPMI1640 medium (GIBCO) supplemented with 10% FBS, were seeded in 96 well, so that each well includes 5000 cells. 24 hours after, the incubated cells were treated with 0.016 ug/ml of L3-1Y/IgG2 antibody prepared in Reference Example 1.

72 hours after the treatment, 100 uL of CellTiter Glo solution (Promega, G7572) was added to each well, and the well was allowed to stay at a room temperature for 30 minutes. The number of cells was counted via luminescence signals, which were recorded using Envision 2104 Multi-label Reader (Perkin Elmer).

Figure 10:
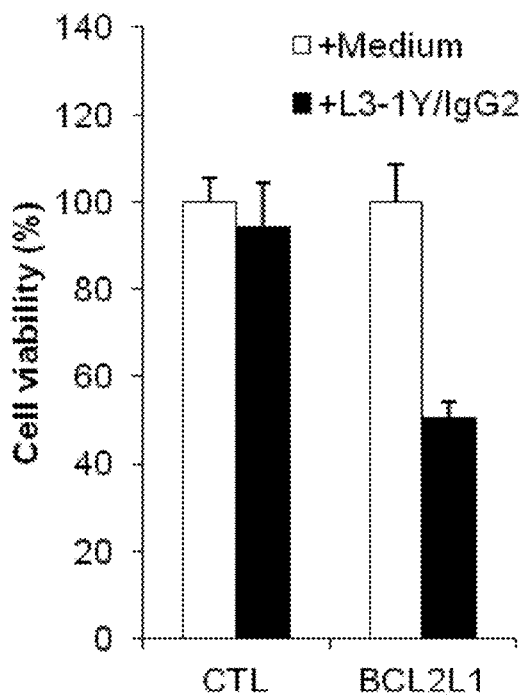
FIG. 10 is a graph showing cell viability of MKN45 gastric cancer cells co-treated with BCL2L1 siRNA and L3-1Y/IgG2 antibody.

The obtained results are illustrated in FIG. 10. As shown in FIG. 10, when L3-1Y/IgG2 antibody was co-treated with BCL2L1 siRNA, the cancer cell growth inhibitory effect of L3-1Y/IgG2 antibody is increased compared to that of the control (CTL: treated with the negative control siRNA).

Example 7

Measurement of Cancer Cell Growth Inhibition by Combination Therapy Using ITGB3 Inhibitor and Anti-c-Met Antibody To verify the effect of the combination therapy using ITGB3 inhibitor and anti-c-Met antibody in a cell on which the anti-c-Met antibody has no effects, breast cancer cells on which the anti-c-Met antibody has no effects and MKN45 gastric cancer cells having an acquired resistance against and anti-c-Met antibody by treatment of and anti-c-Met antibody for at least 3 months, were used.

7.1. Cancer Cell Growth Inhibitory Effect in Breast Cancer Cells

To verify the effect of the combination therapy using ITGB3 inhibitor and anti-c-Met antibody in breast cancer cells on which the anti-c-Met antibody has no effects, HCC1806 (ATCC, CRL-2335) cells were used. The HCC 1806 cells are a cell line known to have high amounts of c-Met.

5000 cells of HCC1806 cells were seeded onto a 96-well plate, and 24 hours after, the plate was treated with L3-1Y/IgG2 antibody and an ITGB3 inhibitor, cilengitide (Merck KGaA, EMD 121974). 72 hours later after the treatment, a change in the number of cells was measured using CellTiter Glo assay. Cilengitide was treated at a fixed concentration of 10 uM, and the L3-1Y/IgG2 antibody was treated by ⅕ dilution each time starting from 2 ug/ml. For comparison, the same test was conducted using L3-1Y/IgG2 antibody alone.

Figure 11:
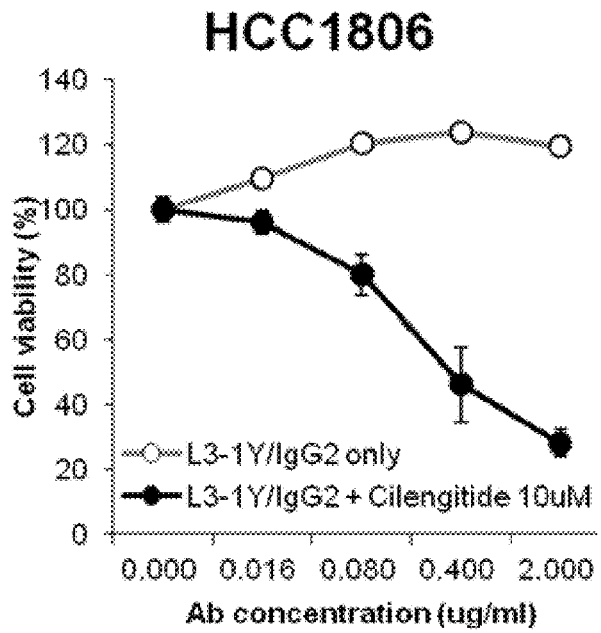
FIG. 11 is a graph showing cell viability of HCC1806 cells co-treated with cilengitide and L3-1Y/IgG2 antibody.

The obtained results are illustrated in FIG. 11. As shown in FIG. 11, when L3-1Y/IgG2 antibody and cilengitide were co-treated, the growth inhibitory effect on HCC1806 cells was exhibited, where such effect did not occur in HCC1806 cell when the cells were treated with the L3-1Y/IgG2 antibody alone. The results show that synergistic effects by the combination administration of cilengitide and L3-1Y/IgG2 antibody in the HCC1806 cells occurred.

7.2. Cancer Cell Growth Inhibitory Effect in L3-1Y/IgG2 Antibody Resistant Cell Line 5000 cells of MKN45 cells which have acquired resistance against L3-1Y/IgG2 antibody were seeded onto a 96-well plate, and 24 hours after, the plate was treated with L3-1Y/IgG2 antibody and an ITGB3 inhibitor, cilengitide (Merck KGaA, EMD 121974). 72 hours later after the treatment, a change in the number of cells was measured using CellTiter Glo assay. The MKN45 cells which have acquired resistance against L3-1Y/IgG2 antibody were prepared referring to Example 4.3. Cilengitide was treated at a fixed concentration of 10 uM, and the L3-1Y/IgG2 antibody was treated by ⅕ dilution each time starting from 2 ug/ml. For comparison, the same test was conducted using L3-1Y/IgG2 antibody alone.

Figure 12:
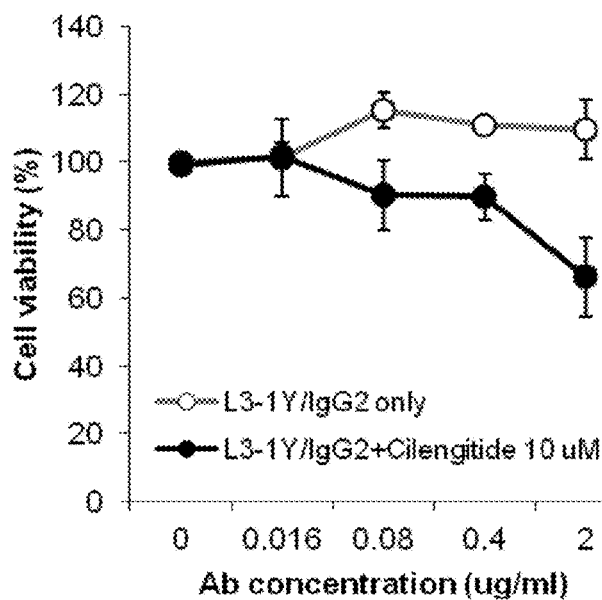
FIG. 12 is a graph showing cell viability of MKN45 gastric cancer cells having an acquired resistance against L3-1Y/IgG2 antibody co-treated with cilengitide and L3-1Y/IgG2 antibody.

The obtained results are illustrated in FIG. 12. As shown in FIG. 12, when L3-1Y/IgG2 antibody and cilengitide were co-treated, the growth inhibitory effect on the L3-1Y/IgG2 antibody resistant MKN45 cells was exhibited, where such effect did not occur when the L3-1Y/IgG2 antibody was treated alone. The results suggest that the acquired resistance against L3-1Y/IgG2 antibody can be overcome by the combination administration of cilengitide and L3-1Y/IgG2 antibody.

Example 8

Measurement of Cancer Cell Growth Inhibition by Combination Therapy Using AKT2 Inhibitor and Anti-c-Met Antibody To verify the effect of the combination therapy using AKT inhibitor and anti-c-Met antibody in a cell on which the anti-c-Met antibody has no effects, breast cancer cells on which the anti-c-Met antibody has no effects and MKN45 gastric cancer cells having an acquired resistance against an anti-c-Met antibody by treatment of an anti-c-Met antibody for at least 3 months, were used.

8.1. Cancer Cell Growth Inhibitory Effect in Breast Cancer Cells

The efficacy of combination administration was examined in a breast cancer cell line on which the anti-c-Met antibody has no effects. For this, HCC1806 (ATCC, CRL-2335) cells were used.

5000 HCC1806 cells were seeded onto a 96-well plate and 24 hours after, the plate was treated with L3-1Y/IgG2 antibody and an AKT inhibitor, MK-2206 (Merck & Co Inc) and 72 hours later after the antibody treatment, a change in the number of cells was measured using CellTiter Glo assay. MK-2206 was treated at a fixed concentration of 10 uM, and the L3-1Y/IgG2 antibody was treated by ⅕ dilution each time starting from 2 ug/ml. For comparison, the same test was conducted using L3-1Y/IgG2 antibody alone.

Figure 13:
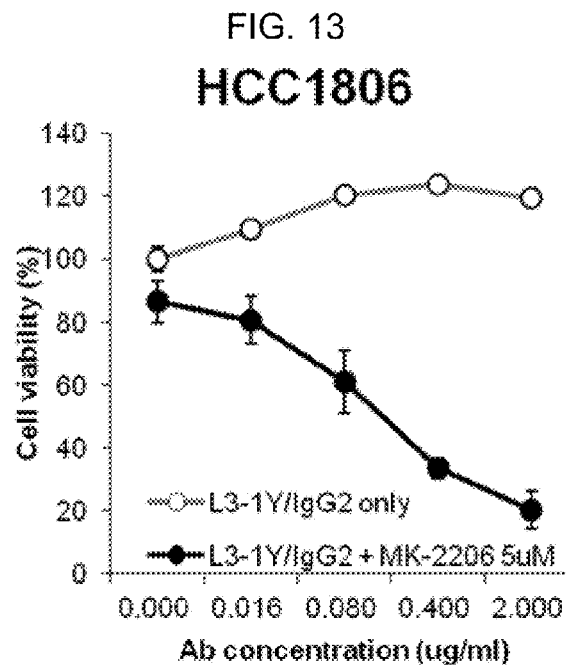
FIG. 13 is a graph showing cell viability of HCC1806 cells co-treated with MK-2206 and L3-1Y/IgG2 antibody.

The obtained result is shown in FIG. 13. As shown in FIG. 13, when the L3-1Y/IgG2 antibody and MK-2206 were co-treated, cancer cell growth inhibitory efficacy which did not occur when treated with the L3-1Y/IgG2 antibody alone was exhibited, and this is to show that there were synergistic effects by the combination administration of MK-2206 and L3-1Y/IgG2 antibody in the HCC1806.

8.2. Cancer Cell Growth Inhibitory Effect in L3-1Y/IgG2 Antibody Resistance Acquired Cell Line 5000 cells of MKN45 cells which have acquired resistance against L3-1Y/IgG2 antibody were seeded onto a 96-well plate, and 24 hours after, the plate was treated with L3-1Y/IgG2 antibody and an AKT inhibitor, MK-2206 (Merck & Co Inc). 72 hours later after the treatment, a change in the number of cells was measured using CellTiter Glo assay. The MKN45 cells which have acquired resistance against L3-1Y/IgG2 antibody were prepared referring to Example 4.3. MK-2206 was treated at a fixed concentration of 5 uM, and the L3-1Y/IgG2 antibody was treated by ⅕ dilution each time starting from 2 ug/ml. For comparison, the same test was conducted using L3-1Y/IgG2 antibody alone.

Figure 14:
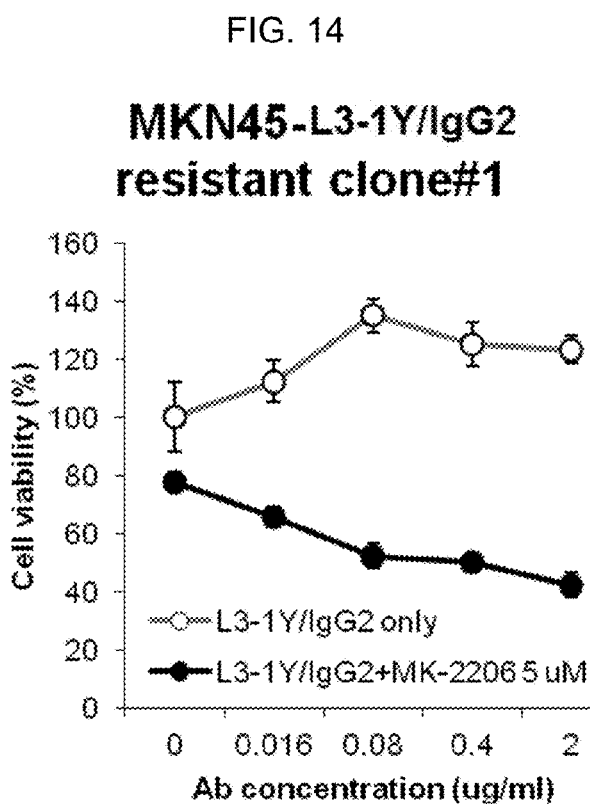
FIG. 14 is a graph showing cell viability of MKN45 gastric cancer cells having an acquired resistance against L3-1Y/IgG2 antibody co-treated with MK-2206 and L3-1Y/IgG2 antibody.

The obtained results are illustrated in FIG. 14. As shown in FIG. 14, when L3-1Y/IgG2 antibody and MK-2206 were co-treated, the growth inhibitory effect on the L3-1Y/IgG2 antibody resistant MKN45 cells was exhibited, where such effect did not occur when the L3-1Y/IgG2 antibody was treated alone. The results suggest that the acquired resistance against L3-1Y/IgG2 antibody can be overcome by the combination administration of MK-2206 and L3-1Y/IgG2 antibody.

Example 9

Measurement of Cancer Cell Growth Inhibition by Combination Therapy Using BCL2L1 Inhibitor and Anti-c-Met Antibody It was examined whether the cancer cell growth inhibition effect of anti-c-Met antibody is increased by BCL2L1 inhibition in various cancer cells.

9.1. Effects in MKN45 Gastric Cancer Cell Line 5000 cells of MKN45 gastric cancer cells were seeded onto a 96-well plate, and 24 hours after, the plate was treated with L3-1Y/IgG2 antibody and a BCL2 family inhibitor, ABT-263 (Abbott Laboratories). 72 hours later after the treatment, a change in the number of cells was measured using CellTiter Glo assay. ABT-263 was treated at a fixed concentration of 5 uM, and the L3-1Y/IgG2 antibody was treated at the concentration of 0.08 ug/ml. For comparison, the same test was conducted using L3-1Y/IgG2 antibody alone or ABT-263 alone.

Figure 15:
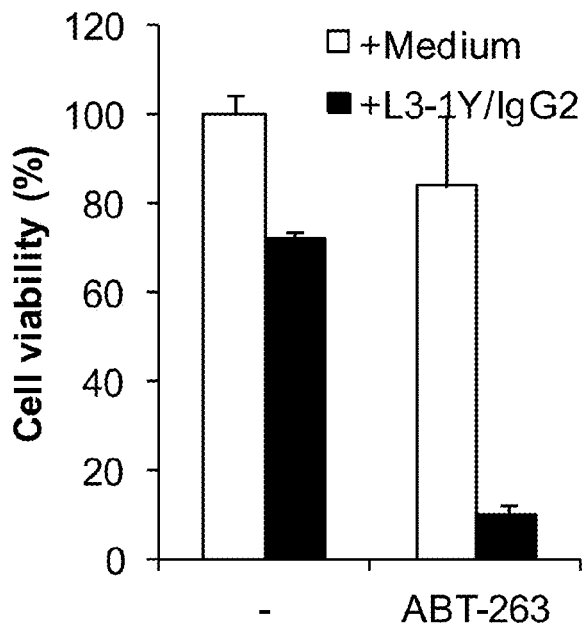
FIG. 15 is a graph showing cell viability of EBC1 lung cancer cells co-treated with a BCL2 inhibitor (ABT-263) and L3-1Y/IgG2 antibody.

The obtained results are illustrated in FIG. 15. As shown in FIG. 15, when L3-1Y/IgG2 antibody and ABT-263 were co-treated, the growth inhibitory effect on MKN45 gastric cancer cells was increased compared to the case that the L3-1Y/IgG2 antibody was treated alone. The results suggest that synergistic effects by the combination administration of ABT-263 and L3-1Y/IgG2 antibody can be achieved in MKN45 gastric cancer cells.

9.2. Effects in Resistance-Acquired MKN45 Gastric Cancer Cell Line

To verify whether or not the resistance acquired by repetitive administration of anti-c-Met antibody can be overcome by BCL2L1 inhibition, L3-1Y/IgG2 antibody resistance acquired MKN45 cells, where the resistance against L3-1Y/IgG2 antibody is acquired by treating MKN45 gastric cancer cells (JCRB, JCRB0254) with the L3-1Y/IgG2 antibody for at least 3 months, were used. The L3-1Y/IgG2 antibody resistance acquired MKN45 gastric cancer cells were prepared referring to Example 4.3.

5000 cells of the L3-1Y/IgG2 antibody resistance acquired MKN45 cells were seeded onto a 96-well plate, and 24 hours after, the plate was treated with a BCL2 family inhibitor, ABT-263 (Abbott Laboratories) and 72 hours later after the antibody treatment, a change in the number of cells was measured using CellTiter Glo assay. ABT-263 was treated at a fixed concentration of 2.5 uM, and the L3-1Y/IgG2 antibody was treated by ⅕ dilution each time starting from 2 ug/ml. For comparison, the same test was conducted using L3-1Y/IgG2 antibody alone.

Figure 16:
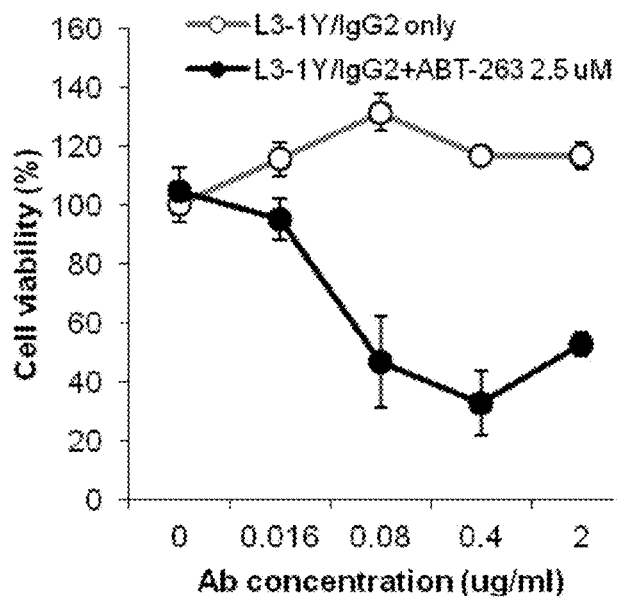
FIG. 16 is a graph showing cell viability of in MKN45 gastric cancer cells having an acquired resistance against L3-1Y/IgG2 antibody co-treated with a BCL2 inhibitor (ABT-263) and L3-1Y/IgG2 antibody.

The obtained result is shown in FIG. 16. As shown in FIG. 16, when the L3-1Y/IgG2 antibody and ABT-263 were co-treated, cancer cell growth inhibitory effect can be achieved, where such effect did not occur when the L3-1Y/IgG2 antibody is treated alone. Such results suggest that by the combination administration of ABT-263 and L3-1Y/IgG2 antibody can lead to synergistic effects in the MKN45 cells which acquired resistance against the L3-1Y/IgG2 antibody.

9.3. Effects in Resistance-Acquired EBC1 Lung Cancer Cell Line

To verify whether or not the resistance acquired by repetitive administration of anti-c-Met antibody can be overcome by BCL2L1 inhibition, L3-1Y/IgG2 antibody resistance acquired EBC1 cells, where the resistance against L3-1Y/IgG2 antibody is acquired by treating EBC1 lung cancer cells (JCRB, JCRB0820) with the L3-1Y/IgG2 antibody for at least 3 months, were used. The L3-1Y/IgG2 antibody resistance acquired EBC1 lung cancer cells were prepared referring to Example 4.3.

5000 cells of the L3-1Y/IgG2 antibody resistance acquired EBC1 cells were seeded onto a 96-well plate and 24 hours after, the plate was treated with a BCL2 family inhibitor, ABT-263 (Abbott Laboratories) and 72 hours later after the antibody treatment, a change in the number of cells was measured using CellTiter Glo assay. ABT-263 was treated at a fixed concentration of 0.5 uM, and the L3-1Y/IgG2 antibody was treated by ⅕ dilution each time starting from 2 ug/ml.

Figure 17:
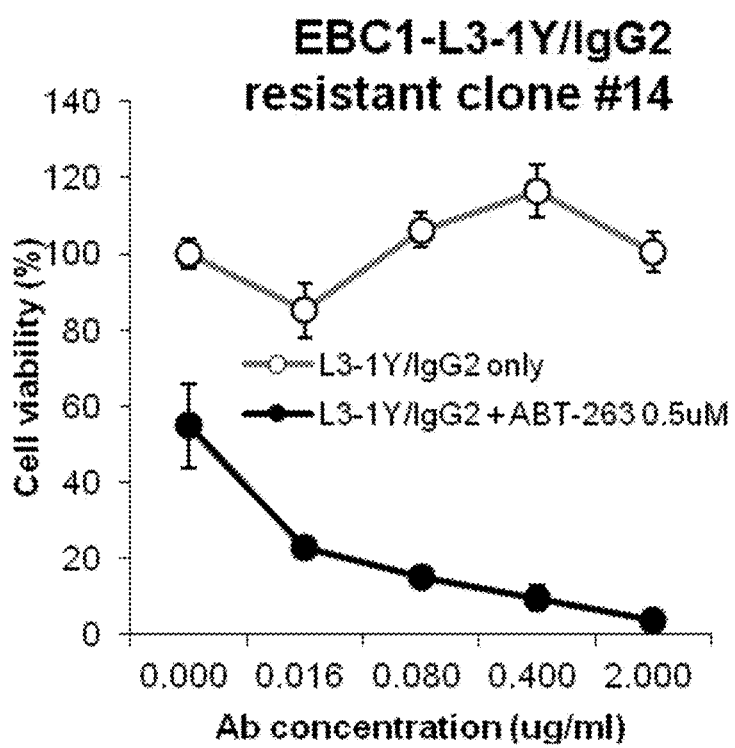
FIG. 17 is a graph showing cell viability of EBC1 lung cancer cells having an acquired resistance against L3-1Y/IgG2 antibody co-treated with a BCL2 inhibitor (ABT-263) and L3-1Y/IgG2 antibody.

The obtained result is shown in FIG. 17. As shown in FIG. 17, when the L3-1Y/IgG2 antibody and ABT-263 were co-treated, cancer cell growth inhibitory effect can be achieved, where such effect did not occur when the L3-1Y/IgG2 antibody is treated alone. Such results show that the combination administration of ABT-263 and L3-1Y/IgG2 antibody can be lead to synergistic effects in the EBC1 cells which acquired resistance against the L3-1Y/IgG2 antibody.

The result suggests that the acquired resistance of the anti-c-Met antibody can be overcome by inhibition of a BCL2 family.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating cancer, comprising co-administering to a subject in need of treating cancer: (a) an anti-c-Met antibody or an antigen-binding fragment thereof, which binds to an epitope comprising 5 to 19 contiguous amino acids of SEQ ID NO: 71, wherein the epitope comprises the amino acid sequence of SEQ ID NO: 73 (EEPSQ), wherein the anti-c-Met antibody or an antigen-binding fragment thereof comprises:

CDR-H1 CDR-H2, CDR-H3, CDR-L1 CDR-L2 and CDR-L3 regions, and the CDR-H1 comprises the amino acid sequence of SEQ ID NOS: 1, 22, 23, or 24, the CDR-H2 comprises the amino acid sequence of SEQ ID NOS: 2, 25, or 26, the CDR-H3 comprises the amino acid sequence of SEQ ID NOS: 3, 27, 28, or 85, the CDR-L1 comprises the amino acid sequence of SEQ ID NOS: 10, 29, 30, 31, 32, 33, or 106, the CDR-L2 comprises the amino acid sequence of SEQ ID NOS: 11, 34, 35, or 36, and the CDR-L3 comprises the amino acid sequence of SEQ ID NOS: 12, 13, 14, 15, 16, 37, 86, or 89; and (b) an inhibitor of a target substance, wherein the target substance is ITGB3 gene or protein encoded thereby.

2. The method according to claim 1, wherein the anti-c-Met antibody or the antigen-binding fragment thereof and the inhibitor against the target substance are co-administered simultaneously.

3. The method according to claim 1, wherein the anti-c-Met antibody or the antigen-binding fragment thereof and the inhibitor against the target substance are co-administered simultaneously or sequentially in any order.

4. The method according to claim 1, wherein the inhibitor against the target substance is at least one selected from the group consisting of a chemical drug, siRNA, shRNA, antibodies, and aptamers against the target substance.

5. The method according to claim 1, wherein the anti-c-Met antibody or an antigen-binding fragment thereof comprises a heavy chain variable region and a light chain variable region, and the heavy chain variable region comprises an amino acid sequence selected from the group consisting of SEQ ID NOS: 17, 74, 87, 90, 91, 92, 93, and 94, and the light chain variable region comprises an amino acid sequence selected from the group consisting of SEQ ID NOS: 109, 18, 19, 20, 21, 75, 88, 95, 96, 97, 98, 99, and 107.

6. The method according to claim 1, wherein the anti-c-Met antibody comprises a heavy chain comprising the amino acid sequence of SEQ ID NO: 62, the amino acid sequence from the 18$^{th}$ to 462$^{nd}$ positions of SEQ ID NO: 62, the amino acid sequence of SEQ ID NO: 64, the amino acid sequence from the 18$^{th}$ to 461$^{st}$ positions of SEQ ID NO: 64, the amino acid sequence of SEQ ID NO: 66, or the amino acid sequence from the 18$^{th}$ to 460$^{th}$ positions of SEQ ID NO: 66; and a light chain comprising the amino acid sequence of SEQ ID NO: 68, the amino acid sequence from the 21$^{st}$ to 240$^{th}$ positions of SEQ ID NO: 68, the amino acid sequence of SEQ ID NO: 70, the amino acid sequence from the 21$^{st}$ to 240$^{th}$ positions of SEQ ID NO: 70, or the amino acid sequence of SEQ ID NO: 108.

* * * * *

Disclaimer

9,567,641 B2 — Bo Gyou Kim, Seoul (KR); Shangzi Wang, Washington, DC (US); Ji Min Lee, Seoul (KR); Kyung Ah Kim, Seongnam-si (KR); Louis M. Weiner, Washington, DC (US). COMBINATION THERAPY FOR THE TREATMENT OF CANCER USING AN ANTI-C-MET ANTIBODY. Patent dated February 14, 2017. Disclaimer filed August 6, 2018, by the assignee, Samsung Electronics Co. Inc. and Georgetown University.

Hereby disclaims the term of this patent which would extend beyond U.S. Patent Application Nos. 13/646,589 and 14/081,917.

*(Official Gazette, October 2, 2018)*

SEQUENCE LISTING

```
<160> NUMBER OF SEQ ID NOS: 109

<210> SEQ ID NO 1
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3
```

-continued

```
Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
<220> FEATURE:
<221> NAME/KEY: MOD_RES
<222> LOCATION: (1)..(1)
<223> OTHER INFORMATION: Xaa is Pro or Ser or absent
<220> FEATURE:
<221> NAME/KEY: MOD_RES
<222> LOCATION: (2)..(2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MOD_RES
<222> LOCATION: (3)..(3)
<223> OTHER INFORMATION: Xaa is Asn or Lys
<220> FEATURE:
<221> NAME/KEY: MOD_RES
<222> LOCATION: (4)..(4)
<223> OTHER INFORMATION: Xaa is Ala or Val
<220> FEATURE:
<221> NAME/KEY: MOD_RES
<222> LOCATION: (7)..(7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: MOD_RES
<222> LOCATION: (5)..(5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MOD_RES
<222> LOCATION: (4)..(4)
<223> OTHER INFORMATION: Xaa is His, Arg, Gln or Lys
<220> FEATURE:
```

```
<221> NAME/KEY: MOD_RES
<222> LOCATION: (9)..(9)
<223> OTHER INFORMATION: Xaa is Ser or Trp
<220> FEATURE:
<221> NAME/KEY: MOD_RES
<222> LOCATION: (12)..(12)
<223> OTHER INFORMATION: Xaa is His or Gln
<220> FEATURE:
<221> NAME/KEY: MOD_RES
<222> LOCATION: (13)..(13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MOD_RES
<222> LOCATION: (2)..(2)
<223> OTHER INFORMATION: Xaa is Ala or Gly
<220> FEATURE:
<221> NAME/KEY: MOD_RES
<222> LOCATION: (4)..(4)
<223> OTHER INFORMATION: Xaa is Thr or Lys
<220> FEATURE:
<221> NAME/KEY: MOD_RES
<222> LOCATION: (7)..(7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MOD_RES
<222> LOCATION: (1)..(1)
<223> OTHER INFORMATION: Xaa is Gly, Ala or Gln
<220> FEATURE:
<221> NAME/KEY: MOD_RES
<222> LOCATION: (6)..(6)
<223> OTHER INFORMATION: Xaa is Arg, His, Ser, Ala, Gly or Lys
<220> FEATURE:
<221> NAME/KEY: MOD_RES
<222> LOCATION: (8)..(8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10
```

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

```
Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti
      c-Met humanized antibody(huAbF46-H4))

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
```

<223> OTHER INFORMATION: Synthetic (light chain variable region of
      anti c-Met humanized antibody(huAbF46-H4))

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
                85                  90                  95

Ser Tyr His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Ser Ser Gln Ser Leu Leu Ala Ser
            20                  25                  30

```
Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
               100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26
```

```
Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15

Ala

<210> SEQ ID NO 32
<211> LENGTH: 17
<212> TYPE: PRT
<213> ORGANISM: Artificial Sequence
```

```
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1               5                   10                  15
Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1               5

<210> SEQ ID NO 38
```

```
<211> LENGTH: 1416
<212> TYPE: DNA
<213> ORGANISM: Artificial Sequence
<220> FEATURE:
<223> OTHER INFORMATION: Synthetic (nucleotide sequence of heavy chain of
      chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc     60
cagtgtgagg tgaagctggt ggagtctgga ggaggcttgg tacagcctgg gggttctctg    120
agactctcct gtgcaactc tgggttcacc ttcactgatt actacatgag ctgggtccgc    180
cagcctccag aaaggcact tgagtggttg gtttttatta aaacaaagc taatggttac    240 acaacagagt acagtgcatc tgtgaagggt cggttcacca tctccagaga taattcccaa    300
agcatcctct atcttcaaat ggacacccctg agagctgagg acagtgccac ttattactgt    360
gcaagagata actggtttgc ttactggggc aagggactc tggtcactgt ctctgcagct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc cccatcccg ggaggagatg   1140 accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
```

```
gactccgacg gctccttctt cctctacagc aagctcaccg tggacaagag caggtggcag      1320
caggggaacg tcttctcatg ctccgtgatg catgaggctc tgcacaacca ctacacgcag      1380
aagagcctct ccctgtctcc gggtaaatga ctcgag                                1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic (nucleotide sequence of light chain
      of chAbF46)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

```
gaattcacta gtgattaatt cgccgccacc atgattcac aggcccaggt cctcatgttg        60
ctgctgctat cggtatctgg tacctgtgga gacattttga tgacccagtc tccatcctcc      120
ctgactgtgt cagcaggaga gaaggtcact atgagctgca gtccagtca gagtctttta       180 gctagtggca accaaaataa ctacttggcc tggcaccagc agaaaccagg acgatctcct      240
aaaatgctga taatttgggc atccactagg gtatctggag tccctgatcg cttcataggc      300
agtggatctg ggacggattt cactctgacc atcaacagtg tgcaggctga agatctggct      360
gtttattact gtcagcagtc ctacagcgct ccgctcacgt tcggtgctgg gaccaagctg      420
gagctgaaac gtacggtggc tgcaccatct gtcttcatct tcccgccatc tgatgagcag      480
ttgaaatctg gaactgcctc tgttgtgtgc ctgctgaata acttctatcc cagagaggcc      540
aaagtacagt ggaaggtgga taacgccctc caatcgggta actcccagga gagtgtcaca      600
gagcaggaca gcaaggacag cacctacagc ctcagcagca ccctgacgct gagcaaagca      660
gactacgaga aacacaaagt ctacgcctgc gaagtcaccc atcagggcct gagctcgccc      720
gtcacaaaga gcttcaacag gggagagtgt tgactcgag                             759
```

<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light)

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
```

```
                35                  40                  45
Pro Pro Lys Leu Leu Ile Ile Trp Ala Ser Thr Arg Val Ser Gly Val
     50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Gln Gln
                 85                  90                  95
Ser Tyr Ser Ala Pro Leu Thr Phe Gly Gly Gly Thr Lys Val Glu Ile
                100                 105                 110
Lys Arg Thr Val Ala Ala Pro Ser Val Phe Ile Phe Pro Pro Ser Asp
                115                 120                 125
Glu Gln Leu Lys Ser Gly Thr Ala Ser Val Val Cys Leu Leu Asn Asn
            130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
                180                 185                 190
Glu Lys His Lys Val Tyr Ala Cys Glu Val Thr His Gln Gly Leu Ser
            195                 200                 205
Ser Pro Val Thr Lys Ser Phe Asn Arg Gly Glu Cys
        210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly
 1               5                  10                  15
Asp Arg Val Thr Ile Thr Cys Lys Ser Ser Gln Ser Leu Leu Ala Ser
                20                  25                  30
Gly Asn Gln Asn Asn Tyr Leu Ala Trp His Gln Gln Lys Pro Gly Lys
            35                  40                  45
Ala Pro Lys Met Leu Ile Ile Trp Ala Ser Thr Arg Val Ser Gly Val
     50                  55                  60
Pro Ser Arg Phe Ser Gly Ser Gly Ser Gly Thr Asp Phe Thr Leu Thr
 65                  70                  75                  80
Ile Ser Ser Leu Gln Pro Glu Asp Phe Ala Thr Tyr Tyr Cys Gln Gln
                 85                  90                  95
Ser Tyr Ser Ala Pro Leu Thr Phe Gly Gln Gly Thr Lys Val Glu Ile
                100                 105                 110
Lys Arg Thr Val Ala Ala Pro Ser Val Phe Ile Phe Pro Pro Ser Asp
                115                 120                 125
Glu Gln Leu Lys Ser Gly Thr Ala Ser Val Val Cys Leu Leu Asn Asn
            130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
```

```
                    180                 185                 190
Glu Lys His Lys Val Tyr Ala Cys Glu Val Thr His Gln Gly Leu Ser
            195                 200                 205

Ser Pro Val Thr Lys Ser Phe Asn Arg Gly Glu
            210                 215
```

<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg␣␣gctggagtg gttgggcttt attagaaaca aagctaacgg ttacaccaca     180
gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagccc aaatcttgt      660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct␣␣tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atgactcgag                                     1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca aagctaacgg ttacaccaca     180
```

```
gaatacagtg cgtctgtgaa aggcagattc accatctcaa gagataattc aaagaactca    240
ctgtatctgc aaatgaacag cctgcgtgct gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca gttcaactg gtacgtggac    840 ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgccccat cccgggagga tgaccaag   1080 aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg   1260 aacgtcttct catgctccgt gatgcatgag gctctgcaca accactacac gcagaagagc   1320
ctctccctgt ctccgggtaa atgactcgag                                     1350

<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49
gaggttcagc tggtggagtc tggcggtggc ctggtgcagc caggggggtc actccgtttg     60
tcctgtgcag cttctggctt caccttcact gattactaca tgagctgggt gcgtcaggcc    120
ccgggtaagg gcctggaatg gttgggtttt attagaaaca agctaatgg ttacacaaca    180 gagtacagtg catctgtgaa gggtcgtttc actataagca gagataattc caaaacacac    240
ctgtacctgc agatgaacag cctgcgtgct gaggacactg ccgtctatta ttgtgctaga    300
gataactggt ttgcttactg gggccaaggg actctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca gttcaactg gtacgtggac    840
```

-continued

| | |
|---|---|
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga tgaccaag | 1080 |
| aaccaggtca gcctgacctg cctggtcaaa ggcttctatc ccagcgacat cgccgtggag | 1140 |
| tgggagagca tgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50

| | |
|---|---|
| gacatcgtga tgacccagtc tccagactcc ctggctgtgt ctctgggcga gagggccacc | 60 |
| atcaactgca gtccagcca gagtctttta gctagcggca accaaaataa ctacttagct | 120 |
| tggcaccagc agaaaccagg acagcctcct aagatgctca ttatttgggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51

| | |
|---|---|
| gatattgtga tgacccagac tccactctcc ctgcccgtca cccctggaga gccggcctcc | 60 |
| atctcctgca gtccagtca gagtctttta gctagtggca accaaaataa ctacttggcc | 120 |
| tggcacctgc agaagccagg gcagtctcca cagatgctga tcatttgggc atccactagg | 180 |
| gtatctggag tcccagacag gttcagtggc agtgggtcag gcactgattt cacactgaaa | 240 |
| atcagcaggg tggaggctga ggatgttgga gtttattact gccagcagtc ctacagcgct | 300 |
| ccgctcacgt tcggacaggg taccaagctg gagctcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |

```
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tgactcgag                                                             669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52

```
gacatcgtga tgacccagtc tccagactcc ctggctgtgt ctctgggcga gagggccacc     60
atcaactgca agtccagcca gagtcttta gctagcggca accaaaataa ctacttagct    120
tggtaccagc agaaaccagg acagcctcct aagctgctca ttatttgggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tgactcgag                                                             669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

```
gatatccaga tgacccagtc cccgagctcc ctgtccgcct ctgtgggcga tagggtcacc     60
atcacctgca agtccagtca gagtcttta gctagtggca accaaaataa ctacttggcc    120
tggcaccaac agaaaccagg aaaagctccg aaaatgctga ttatttgggc atccactagg    180
gtatctggag tccttctcg cttctctgga tccgggtctg gacggatt cactctgacc    240 atcagcagtc tgcagccgga agacttcgca acttattact gtcagcagtc ctacagcgct    300
ccgctcacgt tcggacaggg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tgactcgag                                                             669
```

<210> SEQ ID NO 54
<211> LENGTH: 23
<212> TYPE: PRT

-continued

```
<213> ORGANISM: Artificial Sequence
<220> FEATURE:
<223> OTHER INFORMATION: Synthetic (linker between VH and VL)

<400> SEQUENCE: 54

Gly Leu Gly Gly Leu Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of
      huAbF46 antibody)

<400> SEQUENCE: 55
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg gaatggttgg gtttcattag aaacaaggct     180
aacggttaca ctaccgaata ttctgcttct gttaagggta gattcaccat ttctagagac     240
aactctaaga caccttgta  cttgcaaatg aactccttga gagctgaaga tactgctgtt     300
tattactgcg ctagagataa ttggtttgct tattggggtc aaggtacttt ggttactgtt     360
tcttctggcc tcggggggcct cggaggagga ggtagtggcg gaggaggctc cggtggatcc     420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact ggcttggca  tcaacaaaaa ccaggtaaag ctccaaagat gttgattatt     600
tgggcttcta ccagagtttc tggtgttcca tctagatttt ctggttctgg ttccggtact     660 gatttactt  tgaccatttc atccttgcaa ccagaagatt tcgctactta ctactgtcaa     720
caatcttact ctgctccatt gacttttggt caaggtacaa aggtcgaaat caagagagaa     780
ttcggtaagc ctatccctaa ccctctcctc ggtctcgatt ctacgggtgg tggtggatct     840
ggtggtggtg ttctggtgg  tggtggttct caggaactga caactatatg cgagcaaatc     900
ccctcaccaa ctttagaatc gacgccgtac tctttgtcaa cgactactat tttggccaac     960
gggaaggcaa tgcaaggagt ttttgaatat tacaaatcag taacgtttgt cagtaattgc    1020
ggttctcacc cctcaacaac tagcaaaggc agccccataa acacacagta tgtttttga    1080 gtttaaac                                                             1088

<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including
      polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
```

```
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
```

| | | | | | |
|---|---|---|---|---|---|
| acggattaga | agccgccgag | cgggtgacag | ccctccgaag | gaagactctc | ctccgtgcgt | 60 |
| cctcgtcttc | accggtcgcg | ttcctgaaac | gcagatgtgc | ctcgcgccgc | actgctccga | 120 |
| acaataaaga | ttctacaata | ctagctttta | tggttatgaa | gaggaaaaat | tggcagtaac | 180 |
| ctggccccac | aaaccttcaa | atgaacgaat | caaattaaca | accataggat | gataatgcga | 240 |
| ttagtttttt | agccttattt | ctggggtaat | taatcagcga | agcgatgatt | tttgatctat | 300 |
| taacagatat | ataaatgcaa | aaactgcata | accactttaa | ctaatacttt | caacattttc | 360 |
| ggtttgtatt | acttcttatt | caaatgtaat | aaaagtatca | acaaaaaatt | gttaatatac | 420 |
| ctctatactt | taacgtcaag | gagaaaaaac | cccggatcgg | actactagca | gctgtaatac | 480 |
| gactcactat | agggaatatt | aagctaattc | tacttcatac | attttcaatt | aagatgcagt | 540 |
| tacttcgctg | ttttcaata | ttttctgtta | ttgctagcgt | tttagcagaa | gttcaattgg | 600 |
| ttgaatctgg | tggtggtttg | gttcaaccag | gtggttcttt | gagattgtct | tgtgctgctt | 660 |
| ctggttttac | tttcaccgat | tattacatgt | cctgggttag | acaagctcca | ggtaaaggtt | 720 |
| tggaatggtt | gggtttcatt | agaaacaagg | ctaacggtta | cactaccgaa | tattctgctt | 780 |
| ctgttaaggg | tagattcacc | atttctagag | acaactctaa | gaacaccttg | tacttgcaaa | 840 |
| tgaactcctt | gagagctgaa | gatactgctg | tttattactg | cgctagagat | aattggtttg | 900 |
| cttattgggg | tcaaggtact | ttggttactg | tttcttctgg | cctcgggggc | ctcggaggag | 960 |
| gaggtagtgg | cggaggaggc | tccggtggat | ccagcggtgt | gggttccgat | attcaaatga | 1020 |
| cccaatctcc | atcttctttg | tctgcttcag | ttggtgatag | agttaccatt | acttgtaagt | 1080 |
| cctcccaatc | tttgttggct | tctggtaatc | agaacaatta | cttggcttgg | catcaacaaa | 1140 |
| aaccaggtaa | agctccaaag | atgttgatta | tttgggcttc | taccagagtt | tctggtgttc | 1200 |
| catctagatt | ttctggttct | ggttccggta | ctgattttac | tttgaccatt | tcatccttgc | 1260 |
| aaccagaaga | tttcgctact | tactactgtc | aacaatctta | ctctgctcca | ttgacttttg | 1320 |
| gtcaaggtac | aaaggtcgaa | atcaagagag | aattcggtaa | gcctatccct | aaccctctcc | 1380 |

```
tcggtctcga ttctacgggt ggtggtggat ctggtggtgg tggttctggt ggtggtggtt    1440
ctcaggaact gacaactata tgcgagcaaa tcccctcacc aactttagaa tcgacgccgt    1500
actctttgtc aacgactact attttggcca acgggaaggc aatgcaagga gttttttgaat   1560 attacaaatc agtaacgttt gtcagtaatt gcggttctca cccctcaaca actagcaaag    1620
gcagccccat aaacacacag tatgtttttt gagtttaaac ccgctgatct gataacaaca    1680
gtgtagatgt aacaaaatcg actttgttcc cactgtactt ttagctcgta caaaatacaa    1740 tatactttc atttctccgt aaacaacatg ttttcccatg taatatcctt ttctattttt     1800
cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcatttttga   2040
cgaaatttgc tattttgtta gagtctttta caccatttgt ctccacacct ccgcttacat   2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaaagttca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa acatcctcc ttaggttgat    2460 tacgaaacac gccaaccaag tatttcggag tgcctgaact atttttatat gcttttacaa   2520
gacttgaaat tttccttgca ataaccgggt caattgttct ctttctattg ggcacacata   2580 taataccccag caagtcagca tcggaatcta gagcacattc tgcggcctct gtgctctgca  2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctcctttt cttttttcga ccgaatttct tgaagacgaa agggcctcgt   2820
gatacgccta tttttatagg ttaatgtcat gataataatg gtttcttagg acggatcgct   2880
tgcctgtaac ttacacgcgc ctcgtatctt ttaatgatgg aataatttgg gaatttactc   2940
tgtgtttatt tattttatg ttttgtattt ggatttaga aagtaaataa agaaggtaga     3000
agagttacgg aatgaagaaa aaaaaataaa caaaggttta aaaaatttca acaaaaagcg   3060
tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaaggt agtatttgtt   3240
ggcgatcccc ctagagtctt ttacatcttc ggaaaacaaa aactatttt tctttaattt    3300 cttttttac tttctatttt taatttatat atttatatta aaaatttaa attataatta    3360 tttttatagc acgtgatgaa aaggacccag gtggcacttt tcggggaaat gtgcgcggaa   3420
cccctatttg tttatttttc taaatacatt caaatatgta tccgctcatg agacaataac   3480
cctgataaat gcttcaataa tattgaaaaa ggaagagtat gagtattcaa catttccgtg   3540
tcgcccttat tccctttttt gcggcatttt gccttcctgt ttttgctcac ccagaaacgc   3600
tggtgaaagt aaaagatgct gaagatcagt tgggtgcacg agtgggttac atcgaactgg   3660
atctcaacag cggtaagatc cttgagagtt ttcgccccga agaacgtttt ccaatgatga   3720
gcacttttaa agttctgcta tgtggcgcgg tattatcccg tgttgacgcc gggcaagagc   3780
```

```
aactcggtcg ccgcatacac tattctcaga atgacttggt tgagtactca ccagtcacag   3840
aaaagcatct tacggatggc atgacagtaa gagaattatg cagtgctgcc ataaccatga   3900
gtgataacac tgcggccaac ttacttctga caacgatcgg aggaccgaag gagctaaccg   3960
cttttttgca caacatgggg gatcatgtaa ctcgccttga tcgttgggaa ccggagctga   4020
atgaagccat accaaacgac gagcgtgaca ccacgatgcc tgtagcaatg gcaacaacgt   4080
tgcgcaaact attaactggc gaactactta ctctagcttc ccggcaacaa ttaatagact   4140
ggatggaggc ggataaagtt gcaggaccac ttctgcgctc ggcccttccg gctggctggt   4200
ttattgctga taaatctgga gccggtgagc gtgggtctcg cggtatcatt gcagcactgg   4260
ggccagatgg taagccctcc cgtatcgtag ttatctacac gacgggcagt caggcaacta   4320
tggatgaacg aaatagacag atcgctgaga taggtgcctc actgattaag cattggtaac   4380
tgtcagacca gtttactcat tatatacttt agattgattt aaaacttcat ttttaattta   4440
aaaggatcta ggtgaagatc cttttttgata atctcatgac caaaatccct taacgtgagt   4500
tttcgttcca ctgagcgtca gaccccgtag aaaagatcaa aggatcttct tgagatcctt   4560
ttttttctgcg cgtaatctgc tgcttgcaaa caaaaaaacc accgctacca gcggtggttt   4620
gtttgccgga tcaagagcta ccaactcttt ttccgaaggt aactggcttc agcagagcgc   4680
agataccaaa tactgtcctt ctagtgtagc cgtagttagg ccaccacttc aagaactctg   4740
tagcaccgcc tacatacctc gctctgctaa tcctgttacc agtggctgct gccagtggcg   4800
ataagtcgtg tcttaccggg ttggactcaa gacgatagtt accggataag gcgcagcggt   4860
cgggctgaac ggggggttcg tgcacacagc ccagcttgga gcgaacgacc tacaccgaac   4920
tgagatacct acagcgtgag cattgagaaa gcgccacgct tcccgaaggg agaaaggcgg   4980
acaggtatcc ggtaagcggc agggtcggaa caggagagcg cacgagggag cttccagggg   5040
ggaacgcctg gtatctttat agtcctgtcg ggtttcgcca cctctgactt gagcgtcgat   5100
ttttgtgatg ctcgtcaggg gggccgagcc tatggaaaaa cgccagcaac gcggcctttt   5160
tacggttcct ggccttttgc tggccttttg ctcacatgtt ctttcctgcg ttatccctg   5220
attctgtgga taaccgtatt accgcctttg agtgagctga taccgctcgc cgcagccgaa   5280
cgaccgagcg cagcgagtca gtgagcgagg aagcggaaga gcgcccaata cgcaaaccgc   5340
ctctccccgc gcgttggccg attcattaat gcagctggca cgacaggttt cccgactgga   5400
aagcgggcag tgagcgcaac gcaattaatg tgagttacct cactcattag gcaccccagg   5460
ctttacactt tatgcttccg gctcctatgt tgtgtggaat tgtgagcgga taacaatttc   5520
acacaggaaa cagctatgac catgattacg ccaagctcgg aattaaccct cactaagggg   5580
aacaaaagct ggctagt                                                   5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1               5                   10

<210> SEQ ID NO 58
<211> LENGTH: 435

```
<212> TYPE: DNA
<213> ORGANISM: Artificial Sequence
<220> FEATURE:
<223> OTHER INFORMATION: Synthetic (polynucleotide encoding CDR-L3
      derived from L3-1 clone)

<400> SEQUENCE: 58
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtcagcagtc ctacagccgc ccgtacacgt tcggacaggg taccaaggtg     420
gagatcaaac gtacg                                                      435

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-2 clone)

<400> SEQUENCE: 59
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtgggcagtc ctacagccgt ccgctcacgt tcggacaggg taccaaggtg     420
gagatcaaac gtacg                                                      435

<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-3 clone)

<400> SEQUENCE: 60
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtgcacagtc ctacagccat ccgttctctt tcggacaggg taccaaggtg     420
gagatcaaac gtacg                                                      435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-5 clone)

<400> SEQUENCE: 61

```
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtcagcagtc ctacagccgc ccgtttacgt tcggacaggg taccaaggtg     420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy chain of huAbF46-H4-A1, U6-HC7 hinge and constant region of human IgG1)

<400> SEQUENCE: 62

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220
```

Asn Thr Lys Val Asp Lys Val Glu Pro Lys Ser Cys Asp Cys His
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
    275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
    435                 440                 445

Asn His Tyr Thr Gln Lys Ser Leu Ser Leu Ser Pro Gly Lys
    450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, U6-HC7 hinge
      and constant region of human IgG1)

<400> SEQUENCE: 63
gaattcgccg ccaccatgga atggagctgg gttttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata actggtttgc ttactggggc caagggactc tggtcaccgt ctcctcggct     420
agcaccaagg gcccatcggt cttccccctg gcaccctcct ccaagagcac ctctggggc     480 acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660

```
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga tgaccaag    1140 aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atgactcgag                                    1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region
      of human IgG1)

<400> SEQUENCE: 64

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
                20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser

| | | | | | | | 210 | | | | 215 | | | | 220 | | | |
|---|---|---|---|---|---|---|---|---|---|---|---|---|---|---|---|---|---|---|
Asn Thr Lys Val Asp Lys Lys Val Glu Arg Lys Cys Cys Val Glu Cys
225 230 235 240

Pro Pro Cys Pro Ala Pro Glu Leu Leu Gly Gly Pro Ser Val Phe Leu
245 250 255

Phe Pro Pro Lys Pro Lys Asp Thr Leu Met Ile Ser Arg Thr Pro Glu
260 265 270

Val Thr Cys Val Val Val Asp Val Ser His Glu Asp Pro Glu Val Lys
275 280 285

Phe Asn Trp Tyr Val Asp Gly Val Glu Val His Asn Ala Lys Thr Lys
290 295 300

Pro Arg Glu Glu Gln Tyr Asn Ser Thr Tyr Arg Val Val Ser Val Leu
305 310 315 320

Thr Val Leu His Gln Asp Trp Leu Asn Gly Lys Glu Tyr Lys Cys Lys
325 330 335

Val Ser Asn Lys Ala Leu Pro Ala Pro Ile Glu Lys Thr Ile Ser Lys
340 345 350

Ala Lys Gly Gln Pro Arg Glu Pro Gln Val Tyr Thr Leu Pro Pro Ser
355 360 365

Arg Glu Glu Met Thr Lys Asn Gln Val Ser Leu Thr Cys Leu Val Lys
370 375 380

Gly Phe Tyr Pro Ser Asp Ile Ala Val Glu Trp Glu Ser Asn Gly Gln
385 390 395 400

Pro Glu Asn Asn Tyr Lys Thr Thr Pro Pro Val Leu Asp Ser Asp Gly
405 410 415

Ser Phe Phe Leu Tyr Ser Lys Leu Thr Val Asp Lys Ser Arg Trp Gln
420 425 430

Gln Gly Asn Val Phe Ser Cys Ser Val Met His Glu Ala Leu His Asn
435 440 445

His Tyr Thr Gln Lys Ser Leu Ser Leu Ser Pro Gly Lys
450 455 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
    consisting of heavy chain of huAbF46-H4-A1, human IgG2
    hinge and constant region of human IgG1)

<400> SEQUENCE: 65
gaattcgccg ccaccatgga atggagctgg gttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata ctggtttgc ttactggggc caagggactc tggtcaccgt ctcctcggct    420
agcaccaagg gcccatcggt cttcccctg gcaccctcct ccaagagcac ctctggggc    480 acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600

```
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgcccccc ctgcccagca cctgaactcc tggggggacc gtcagtcttc    780
ctcttccccc caaaacccaa ggacaccctc atgatctccc ggaccctga ggtcacatgc      840 gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg actcgag                                        1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region
      of human IgG2)

<400> SEQUENCE: 66

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205
```

Asn Phe Gly Thr Gln Thr Tyr Thr Cys Asn Val Asp His Lys Pro Ser
    210                 215                 220
Asn Thr Lys Val Asp Lys Thr Val Glu Arg Lys Cys Cys Val Glu Cys
225                 230                 235                 240
Pro Pro Cys Pro Ala Pro Pro Val Ala Gly Pro Ser Val Phe Leu Phe
                245                 250                 255
Pro Pro Lys Pro Lys Asp Thr Leu Met Ile Ser Arg Thr Pro Glu Val
                260                 265                 270
Thr Cys Val Val Val Asp Val Ser His Glu Asp Pro Glu Val Gln Phe
            275                 280                 285
Asn Trp Tyr Val Asp Gly Val Glu Val His Asn Ala Lys Thr Lys Pro
    290                 295                 300
Arg Glu Glu Gln Phe Asn Ser Thr Phe Arg Val Val Ser Val Leu Thr
305                 310                 315                 320
Val Val His Gln Asp Trp Leu Asn Gly Lys Glu Tyr Lys Cys Lys Val
                325                 330                 335
Ser Asn Lys Gly Leu Pro Ala Pro Ile Glu Lys Thr Ile Ser Lys Thr
                340                 345                 350
Lys Gly Gln Pro Arg Glu Pro Gln Val Tyr Thr Leu Pro Pro Ser Arg
            355                 360                 365
Glu Glu Met Thr Lys Asn Gln Val Ser Leu Thr Cys Leu Val Lys Gly
    370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Met Leu Asp Ser Asp Gly Ser
                405                 410                 415
Phe Phe Leu Tyr Ser Lys Leu Thr Val Asp Lys Ser Arg Trp Gln Gln
            420                 425                 430
Gly Asn Val Phe Ser Cys Ser Val Met His Glu Ala Leu His Asn His
    435                 440                 445
Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2
      hinge and constant region of human IgG2)

<400> SEQUENCE: 67
gaattcgccg ccaccatgga atggagctgg ttttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta agcagaga taattccaaa      300 aacacactgt acctgcagat gaacagcctg cgtgctgagg acactgccgt ctattattgt     360
gctagagata actggtttgc ttactggggc caagggactc tggtcaccgt ctcctcggct     420
agcaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600

```
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa acccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caagggcag    1080 ccccgagaac cacaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                         1404

<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1(H36Y) and human kappa constant region)

<400> SEQUENCE: 68

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp Tyr Gln Gln
        50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205
```

```
Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic (polynucleotide encoding polypeptide consisting of light chain of huAbF46-H4-A1(H36Y) and human kappa constant region)

<400> SEQUENCE: 69

```
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtcttttag     180
ctagtggcaa ccaaaataac tacttggcct ggtaccaaca gaaaccagga aaagctccga     240
aaatgctgat tatttgggca tccactaggg tatctggagt cccttctcgc ttctctggat     300
ccgggtctgg gacggatttc actctgacca tcagcagtct gcagccggaa gacttcgcaa     360
cttattactg tcagcagtcc tacagccgcc cgtacacgtt cggacagggt accaaggtgg     420
agatcaaacg tacggtggct gcaccatctg tcttcatctt cccgccatct gatgagcagt     480
tgaaatctgg aactgcctct gttgtgtgcc tgctgaataa cttctatccc agagaggcca     540
aagtacagtg gaaggtggat aacgcccctcc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                              758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic (polypeptide consisting of light chain of huAbF46-H4-A1 and human kappa constant region)

<400> SEQUENCE: 70

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp His Gln Gln
        50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125
```

```
Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of
      anti-c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30
```

-continued

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
                100                 105                 110

Val Thr Val Ser Ser
            115

<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody (AbF46 or huAbF46-H1))

<400> SEQUENCE: 75

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
                20                  25                  30

Gly Asn Gln Asn Asn Tyr Leu Ala Trp His Gln Gln Lys Pro Gly Gln
            35                  40                  45

Pro Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
                100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)

<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76

```
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag gaaaggcact gagtggttg ggttttatta gaaacaaagc taatggttac    240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc aagggactc tggtcactgt ctctgcagct    420
agcaccaagg gcccatcggt cttccccctg gcaccctcct ccaagagcac ctctggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic (nucleotide sequence of light chain
      of anti-c-Met antibody (AbF46 or huAbF46-H1))
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)

```
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77
gaattcacta gtgattaatt cgccgccacc atgattcac aggcccaggt cctcatgttg      60
ctgctgctat cggtatctgg tacctgtgga gacattttga tgacccagtc tccatcctcc    120
ctgactgtgt cagcaggaga aaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759

<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met
      protein)

<400> SEQUENCE: 78
atgaaggccc ccgctgtgct tgcacctggc atcctcgtgc tcctgtttac cttggtgcag    60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg gaacacccag attgtttccc atgtcaggac    300
tgcagcagca agccaatttt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca cagtcggag gttcactgc     480
atattctccc cacagataga agagccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
```

```
gaaacgaaag atggttttat gttttgacg gaccagtcct acattgatgt tttacctgag      720
ttcagagatt cttaccccat taagtatgtc catgcctttg aaagcaacaa ttttatttac      780
ttcttgacgg tccaaaggga aactctagat gctcagactt tcacacaag aataatcagg       840 ttctgttcca taaactctgg attgcattcc tacatggaaa tgcctctgga gtgtattctc      900
acagaaaaga gaaaaagag atccacaaag aaggaagtgt ttaatatact tcaggctgcg      960
tatgtcagca agcctgggc ccagcttgct agacaaatag gagccagcct gaatgatgac     1020
attcttttcg gggtgttcgc acaaagcaag ccagattctg ccgaaccaat ggatcgatct     1080
gccatgtgtg cattccctat caaatatgtc aacgacttct tcaacaagat cgtcaacaaa     1140
aacaatgtga gatgtctcca gcattttac ggacccaatc atgagcactg ctttaatagg      1200
acacttctga gaaattcatc aggctgtgaa gcgcgccgtg atgaatatcg aacagagttt     1260
accacagctt tgcagcgcgt tgacttattc atgggtcaat tcagcgaagt cctcttaaca     1320
tctatatcca ccttcattaa aggagacctc accatagcta atcttgggac atcagagggt     1380
cgcttcatgc aggttgtggt ttctcgatca ggaccatcaa cccctcatgt gaattttctc     1440
ctggactccc atccagtgtc tccagaagtg attgtggagc atacattaaa ccaaaatggc     1500
tacacactgg ttatcactgg gaagaagatc acgaagatcc cattgaatgg cttgggctgc     1560
agacatttcc agtcctgcag tcaatgcctc tctgccccac cctttgttca gtgtggctgg     1620
tgccacgaca aatgtgtgcg atcggaggaa tgcctgagcg gacatggac tcaacagatc       1680 tgtctgcctg caatctacaa ggttttccca aatagtgcac cccttgaagg agggacaagg     1740
ctgaccatat gtggctggga ctttggattt cggaggaata taaatttga tttaaagaaa      1800 actagagttc tccttggaaa tgagagctgc accttgactt taagtgagag cacgatgaat     1860
acattgaaat gcacagttgg tcctgccatg aataagcatt tcaatatgtc cataattatt     1920
tcaaatggcc acgggacaac acaatacagt acattctcct atgtggatcc tgtaataaca     1980
agtatttcgc cgaaatacgg tcctatggct ggtggcactt tacttacttt aactggaaat     2040
tacctaaaca gtgggaattc tagacacatt tcaattggtg gaaaaacatg tactttaaaa     2100
agtgtgtcaa acagtattct tgaatgttat accccagccc aaaccatttc aactgagttt     2160
gctgttaaat tgaaaattga cttagccaac cgagagacaa gcatcttcag ttaccgtgaa     2220
gatcccattg tctatgaaat tcatccaacc aaatctttta ttagtggtgg agcacaata     2280 acaggtgttg ggaaaaacct gaattcagtt agtgtcccga gaatggtcat aaatgtgcat     2340
gaagcaggaa ggaactttac agtggcatgt caacatcgct ctaattcaga gataatctgt     2400
tgtaccactc cttccctgca acagctgaat ctgcaactcc cctgaaaaac caaagccttt     2460
ttcatgttag atgggatcct ttccaaatac tttgatctca tttatgtaca taatcctgtg     2520
tttaagcctt ttgaaaagcc agtgatgatc tcaatgggca atgaaaatgt actggaaatt     2580
aagggaaatg atattgaccc tgaagcagtt aaaggtgaag tgttaaagt tggaaataag     2640 agctgtgaga atatacactt acattctgaa gccgttttat gcacggtccc caatgacctg     2700
ctgaaattga acagcgagct aaatatagag tggaagcaag caatttcttc aaccgtcctt     2760
ggaaaagtaa tagttcaacc agatcagaat ttcacaggat tgattgctgg tgttgtctca     2820
atatcaacag cactgttatt actacttggg ttttcctgt ggctgaaaaa gagaaagcaa      2880
attaaagatc tgggcagtga attagttcgc tacgatgcaa gagtacacac tcctcatttg     2940
gataggcttg taagtgcccg aagtgtaagc ccaactacag aaatggtttc aaatgaatct     3000
gtagactacc gagctacttt tccagaagat cagtttccta attcatctca gaacggttca     3060
```

-continued

```
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg aatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacacctttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctactatgt gaacgtaaaa    4080
tgtgtcgctc cgtatccttc tctgttgtca tcagaagata cgctgatga tgaggtggac    4140
acacgaccag cctccttctg ggagacatca                                      4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

```
Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160
```

```
Arg Arg Leu Lys Glu Thr Lys Asp Gly Phe Met Leu Thr Asp Gln
            165                 170                 175

Ser Tyr Ile Asp Val Leu Pro Glu Phe Arg Asp Ser Tyr Pro Ile Lys
        180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
        210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Ile Leu Phe Gly
            275                 280                 285

Val Phe Ala Gln Ser Lys Pro Asp Ser Ala Glu Pro Met Asp Arg Ser
            290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
            370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
            435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80
```

```
Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
    370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)
```

<400> SEQUENCE: 81

```
Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain of c-Met)

<400> SEQUENCE: 82

```
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
```

```
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tgggagccaa agtcctttca tctgtaaagg accggttcat caacttcttt     420
gtaggcaata ccataaattc ttcttatttc ccagatcatc cattgcattc gatatcagtg     480
agaaggctaa aggaaacgaa agatggtttt atgtttttga cggaccagtc ctacattgat     540
gttttacctg agttcagaga ttcttacccc attaagtatg tccatgcctt tgaaagcaac     600
aattttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa agaaggaagt gtttaatata     780
cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccccctcat  1260 gtgaattttc tcctggactc ccatccagtg tctccagaag tgattgtgga gcatacatta    1320
aaccaaaatg gc                                                         1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT
      domain of c-Met)

<400> SEQUENCE: 83

```
tacacactgg ttatcactgg gaagaagatc acgaagatcc cattgaatgg cttgggctgc      60
agacatttcc agtcctgcag tcaatgcctc tctgccccac cctttgttca gtgtggctgg     120
tgccacgaca aatgtgtgcg atcggaggaa tgcctgagcg ggacatggac tcaacagatc     180
tgtctgcctg caatctacaa ggttttccca aatagtgcac cccttgaagg agggacaagg     240
ctgaccatat gtggctggga ctttggattt cggaggaata taaatttga tttaaagaaa     300 actagagttc tccttggaaa tgagagctgc accttgactt aagtgagag cacgatgaat     360 acattgaaat gcacagttgg tcctgccatg aataagcatt tcaatatgtc cataattatt     420
tcaaatggcc acgggacaac acaatacagt acattctcct atgtggatcc tgtaataaca     480
agtatttcgc cgaaatacgg tcctatggct ggtggcactt tacttacttt aactggaaat     540
tacctaaaca gtgggaattc tagacacatt tcaattggtg gaaaaacatg tacttttaaa     600
agtgtgtcaa acagtattct tgaatgttat accccagccc aaaccatttc aactgagttt     660
gctgttaaat tgaaaattga cttagccaac cgagagacaa gcatcttcag ttaccgtgaa     720
gatcccattg tctatgaaat tcatccaacc aaatctttta ttagtggtgg agcacaata     780 acaggtgttg ggaaaaacct gaattcagtt agtgtcccga gaatggtcat aaatgtgcat    840
```

```
gaagcaggaa ggaactttac agtggcatgt caacatcgct ctaattcaga gataatctgt      900
tgtaccactc cttccctgca acagctgaat ctgcaactcc ccctgaaaac caaagccttt      960
ttcatgttag atgggatcct ttccaaatac tttgatctca tttatgtaca taatcctgtg     1020
tttaagccct ttgaaaagcc agtgatgatc tcaatgggca atgaaaatgt actggaaatt     1080
aagggaaatg atattgaccc tgaagcagtt aaaggtgaag tgttaaaagt tggaaataag     1140
agctgtgaga atatacactt acattctgaa gccgttttat gcacggtccc caatgacctg     1200
ctgaaattga acagcgagct aaatatagag tggaagcaag caatttcttc aaccgtcctt     1260
ggaaaagtaa tagttcaacc agatcagaat ttcacagga                            1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain
      of c-Met)

<400> SEQUENCE: 84

```
gtgcatttca atgaagtcat aggaagaggg cattttggtt gtgtatatca tgggactttg       60
ttggacaatg atggcaagaa aattcactgt gctgtgaaat ccttgaacag aatcactgac      120
ataggagaag tttcccaatt tctgaccgag ggaatcatca tgaaagattt tagtcatccc      180
aatgtcctct cgctcctggg aatctgcctg cgaagtgaag ggtctccgct ggtggtccta      240
ccatacatga acatggagga tcttcgaaat tcattcgaaa tgagaactca taatccaact      300
gtaaaagatc ttattggctt tggtcttcaa gtagccaaag gcatgaaata tcttgcaagc      360
aaaaagtttg tccacagaga cttggctgca gaaaactgta tgctggatga aaaattcaca      420
gtcaaggttg ctgattttgg tcttgccaga gacatgtatg ataaagaata ctatagtgta      480
cacaacaaaa caggtgcaaa gctgccagtc aagtggatgg cttttgaaag tctgcaaact      540
caaaagttta ccaccaagtc agatgtgtgg tcctttggcg tgctcctctg ggagctgatg      600
acaagaggag cccccacctta tcctgacgta aacacctttg atataactgt ttacttgttg      660
caagggagaa gactcctaca acccgaatac tgcccagacc ccttatatga agtaatgcta      720
aaatgctggc accctaaagc cgaaatgcgc catccttttt ctgaactggt gtcccggata      780
tcagcgatct tctctacttt cattggggag cactatgtcc atgtgaacgc tacttatgtg      840
aacgtaaaat gtgtcgctcc gtatccttct ctgttgtcat cagaagataa cgctgatgat      900
gaggtggaca cacgaccagc ctccttctgg agacatca                             939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met
      antibody)

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence

```
<220> FEATURE:
<223> OTHER INFORMATION: Synthetic (light chain CDR3 of anti-c-Met
      antibody)

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of
      monoclonal antibody AbF46)

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody)

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
                20                  25                  30

Gly Asn Gln Asn Asn Tyr Leu Ala Trp His Gln Gln Lys Pro Gly Arg
            35                  40                  45

Ser Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg
```

-continued

```
<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 89

Gln Gln Ser Tyr Ser Ala Pro Leu Thr Phe Gly Ala Gly Thr Lys Leu
1               5                   10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH1)

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95
```

```
Tyr Cys Ala Arg Asp Asn Trp Phe Ala Tyr Trp Gly Gln Gly Thr Leu
                100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH3)

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 94
<211> LENGTH: 117
```

<212> TYPE: PRT
<213> ORGANISM: Artificial Sequence
<220> FEATURE:
<223> OTHER INFORMATION: Synthetic (heavy chain variable region of AT-VH5)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of anti c-Met humanized antibody(huAbF46-H4))

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of AT-Vk1)

<400> SEQUENCE: 96

Asp Ile Leu Met Thr Gln Ser Pro Ser Ser Leu Thr Ala Ser Val Gly
1               5                   10                  15

-continued

```
Asp Arg Val Thr Met Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of
      AT-Vk2)

<400> SEQUENCE: 97

```
Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of
      AT-Vk3)

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
```

```
                        65                  70                  75                  80
Ile Ser Ser Leu Gln Ala Glu Asp Val Ala Val Tyr Tyr Cys Gln Gln
                    85                  90                  95

Ser Tyr Ser Ala Pro Leu Thr Phe Gly Gln Gly Thr Lys Leu Glu Ile
                100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of
      AT-Vk4)

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
                100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102
```

```
<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))

<400> SEQUENCE: 103

Glu Arg Lys Cys Cys Val Glu Cys Pro Pro Cys Pro
1               5                   10
```

```
Glu Pro Arg Asp Cys Gly Cys Lys Pro Cys Pro Pro Cys Pro
1               5                   10
```

```
<210> SEQ ID NO 104
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1               5                   10
```

```
<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1               5                   10                  15
```

```
<210> SEQ ID NO 106
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

Lys Ser Ser Gln Ser Leu Leu Ala Trp Gly Asn Gln Asn Asn Tyr Leu
1               5                   10                  15

Ala
```

```
<210> SEQ ID NO 107
<211> LENGTH: 114
<212> TYPE: PRT
<213> ORGANISM: Artificial Sequence
<220> FEATURE:
<223> OTHER INFORMATION: Synthetic (amino acid sequence of light chain
      variable region of antibody L3-11Y)

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
```

```
                    50                  55                  60
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
                100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic (amino acid sequence of light chain
      of antibody L3-11Y)

<400> SEQUENCE: 108

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
                 20                  25                  30

Gly Asn Gln Asn Asn Tyr Leu Ala Trp Tyr Gln Gln Lys Pro Gly Lys
             35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
             115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
195                 200                 205

Ser Pro Val Thr Lys Ser Phe Asn Arg Gly Glu Cys
210                 215                 220

<210> SEQ ID NO 109
<211> LENGTH: 114
<212> TYPE: PRT
<213> ORGANISM: Artificial Sequence
<220> FEATURE:
<223> OTHER INFORMATION: light chain variable region of anti c-Met
      antibody

<400> SEQUENCE: 109

Asp Ile Gln Met Thr Gln Ser Pro Ser Ser Leu Ser Ala Ser Val Gly
 1               5                  10                  15
```

```
Asp Arg Val Thr Ile Thr Cys Lys Ser Ser Gln Ser Leu Leu Ala Ser
            20              25              30

Gly Asn Gln Asn Asn Tyr Leu Ala Trp Tyr Gln Gln Lys Pro Gly Lys
        35              40              45

Ala Pro Lys Met Leu Ile Ile Trp Ala Ser Thr Arg Val Ser Gly Val
    50              55              60

Pro Ser Arg Phe Ser Gly Ser Gly Ser Gly Thr Asp Phe Thr Leu Thr
65              70              75              80

Ile Ser Ser Leu Gln Pro Glu Asp Phe Ala Thr Tyr Tyr Cys Gln Gln
            85              90              95

Ser Tyr Ser Arg Pro Tyr Thr Phe Gly Gln Gly Thr Lys Val Glu Ile
            100             105             110

Lys Arg
```